US010238470B2

(12) United States Patent
Burton

(10) Patent No.: US 10,238,470 B2
(45) Date of Patent: Mar. 26, 2019

(54) DENTAL WEDGES AND MATRIX BANDS FOR USE IN DIRECT COMPOSITE RESTORATION TECHNIQUES FOR POSTERIOR TEETH

(71) Applicant: Burton Dental Innovations, LLC, Hinsdale, IL (US)

(72) Inventor: Matthew Burton, Hinsdale, IL (US)

(73) Assignee: Burton Dental Innovations, LLC, Hinsdale, IL (US)

( * ) Notice: Subject to any disclaimer, the term of this patent is extended or adjusted under 35 U.S.C. 154(b) by 0 days.

(21) Appl. No.: 15/727,548

(22) Filed: Oct. 6, 2017

(65) Prior Publication Data
US 2018/0098824 A1 Apr. 12, 2018

Related U.S. Application Data

(60) Provisional application No. 62/462,712, filed on Feb. 23, 2017, provisional application No. 62/434,229, (Continued)

(51) Int. Cl.
| | |
|---|---|
| A61C 5/00 | (2017.01) |
| A61C 5/85 | (2017.01) |
| A61C 5/88 | (2017.01) |
| A61C 3/06 | (2006.01) |
| A61C 5/60 | (2017.01) |

(52) U.S. Cl.
CPC ............... *A61C 5/85* (2017.02); *A61C 3/06* (2013.01); *A61C 5/88* (2017.02); *A61C 5/60* (2017.02)

(58) Field of Classification Search
CPC .... A61C 5/85; A61C 5/88; A61C 3/06; A61C 5/60
See application file for complete search history.

(56) References Cited

U.S. PATENT DOCUMENTS

| 3,815,243 A | 6/1974 | Eames |
| 4,997,367 A * | 3/1991 | Kassel .................. A61C 5/85 433/226 |

(Continued)

FOREIGN PATENT DOCUMENTS

| DE | 3816501 A1 | 11/1989 |
| EP | 1541092 A2 | 6/2005 |
| WO | WO-2014/060020 A1 | 4/2014 |

OTHER PUBLICATIONS dentsplysirona.com, "AutoMatrix® Retainerless Matrix System," (2003). Retrieved from the Internet on Jan. 8, 2018: https://www.dentsplysirona.com/content/dam/dentsply/pim/manufacturer/Restorative/Accessories/Matrix_Systems/Sectional_Systems/Palodent_Sectional_Matrix_System/AutoMatrix-Palodent-txtken0-en-1402.
(Continued)

*Primary Examiner* — Nicholas D Lucchesi
(74) *Attorney, Agent, or Firm* — Marshall, Gerstein & Borun LLP

(57) ABSTRACT

A wedge system for use in a dental restoration procedure for a posterior tooth. The wedge system includes a first wedge including a body, a first arm extending from the body, a second arm extending from the body, and a gap formed between the first arm and the second arm. In some cases, the wedge system may include a second wedge including a body and an arm extending from the body, and at least a portion of the arm of the second wedge can be disposed in the gap of the first wedge to removably secure the second wedge to the first wedge.

19 Claims, 18 Drawing Sheets

Related U.S. Application Data filed on Dec. 14, 2016, provisional application No. 62/427,669, filed on Nov. 29, 2016, provisional application No. 62/405,099, filed on Oct. 6, 2016.

(56) References Cited

U.S. PATENT DOCUMENTS

| | | | | |
|---|---|---|---|---|
| 5,114,341 | A * | 5/1992 | Kassel | A61C 5/85 433/39 |
| 5,730,592 | A | 3/1998 | Meyer | |
| 6,375,463 | B1 * | 4/2002 | McLean | A61C 5/85 433/149 |
| 6,712,608 | B2 | 3/2004 | Bills | |
| 7,083,412 | B1 * | 8/2006 | Karapetyan | A61C 5/85 433/148 |
| 7,097,452 | B2 | 8/2006 | Friedman | |
| 9,629,693 | B2 * | 4/2017 | McDonald | A61C 5/88 |
| 9,883,922 | B2 | 2/2018 | McDonald | |
| 2003/0113688 | A1 * | 6/2003 | Weissenfluh | A61C 5/88 433/149 |
| 2003/0186186 | A1 * | 10/2003 | Hahn | A61C 5/85 433/39 |
| 2005/0147941 | A1 * | 7/2005 | McDonald | A61C 5/85 433/153 |
| 2006/0084029 | A1 * | 4/2006 | Viscomi | A61C 5/85 433/40 |
| 2007/0087310 | A1 * | 4/2007 | Giusti | A61C 5/85 433/155 |
| 2008/0064000 | A1 * | 3/2008 | Clark | A61C 5/125 433/29 |
| 2009/0029324 | A1 * | 1/2009 | Clark | A61C 5/85 433/226 |
| 2011/0250563 | A1 | 10/2011 | Horvath et al. | |
| 2011/0262878 | A1 * | 10/2011 | Galler | A61C 5/85 433/39 |
| 2011/0306007 | A1 | 12/2011 | Ericson et al. | |
| 2015/0125817 | A1 * | 5/2015 | McDonald | A61C 5/88 433/149 |
| 2015/0150651 | A1 * | 6/2015 | McDonald | A61C 5/88 433/149 |
| 2015/0282896 | A1 * | 10/2015 | Ulso | A61C 5/12 433/148 |

OTHER PUBLICATIONS dentsplysirona.com, "Palodent Plus, Sectional Matrix System, The Shape of Confidence." Retrieved from the Internet on Jan. 8, 2018: https://www.dentsplysirona.com/content/dam/dentsply/pim/manufacturer/Restorative/Accessories/Matrix_Systems/Sectional_Systems/Palodent_Plus_Sectional_Matrix_System/Palodent-Plus-887kmcf-en-1402.

dentsplysirona.com, "The Palodent® System, The original, most trusted, and highest rated contoured section matrix system," (2006). Retrieved from the Internet on Jan. 8, 2018: https://www.dentsplysirona.com/content/dam/dentsply/pim/manufacturer/Restorative/Accessories/Matrix_Systems/Sectional_Systems/Palodent_Sectional_Matrix_System/AutoMatrix-Palodent-3gp9usp-en-1402.

directadental.com, "Clinical Tips: FenderMate Prime protection and matrix for primary teeth." Retrieved from the Internet on Jan. 8, 2018: http://www.directadental.com/products/education/clinical-tips--fendermate-prime.

directadental.com, "FenderMate® Sectional matrix for Class II composite restorations." Retrieved from the Internet on Jan. 8, 2018: http://www.directadental.com/products/restorative/fendermate.

garrisondental.com, "Matrix Bands." Retrieved from the Internet on Jan. 8, 2018: https://garrisondental.com/en/matrix-bands.

pattersondental.com, "Contact Matrix™ System, Thin-Flex Matrices—Danville Materials." Retrieved from the Internet on Jan. 8, 2018: https://www.pattersondental.com/Supplies/ProductFamilyDetails/PIF_62351?mc=0.

pattersondental.com, "Patterson Dental, Patient Experience, Practice Lifestyle," (2018) Patterson Dental Supply, Inc. Retrieved from the Internet on Jan. 9, 2018: https://www.pattersondental.com/Supplies/ProductItemFamily/86095/Retainer-Bands-Wedges?ss=86141.

pinkband.org, "PinkBand® Silicone Coated Dental Matrix Bands," (2014). Retrieved from the Internet on Jan. 8, 2018: http://www.pinkband.org/.

ultradent.com, "The Triodent® Story, Triodent's award-winning range of products," (2017). Retrieved from the Internet on Jan. 8, 2018: https://www.ultradent.com/en-us/Dental-Products-Supplies/Prepare/triodent-matrix-systems/Pages/triodent-story.aspx?s_cid=2024.

ultradent.com, "V3 Blue Quick Guide." Retrieved from the Internet on Jan. 8, 2018: https://www.ultradent.com/en-us/Product%20Instruction%20Documents/V3-Blue.pdf.

net32.com, "Net32, FenderMate Right Regular, Dark Blue 18/PK. Combines a pre-curved," (2018) Net32 Inc. Retrieved from the Internet on Jan. 11, 2018: https://www.net32.com/ec/fendermate-right-regular-dark-blue-18-combines-d-105770?utm_source=Windfall&utm_medium=productfeed&utm_content=dental&utm_campaign=googleshopping&utm_source=google&utm_medium=cpc&adpos=1o2&scid=scplp105770&sc_intid=105770&gclid=Cj0KCQjwpMLOBRC9ARIsAPiGeZD-tkgMGqGENeYrlgSUo47wqMbFgSowyy344K1qT8MBta6TYjMOTaQaAryyEALw_wcB.

International Search Report and Written Opinion of the International Searching Authority for Application No. PCT/US2017/055668, dated Jan. 30, 2018.

* cited by examiner

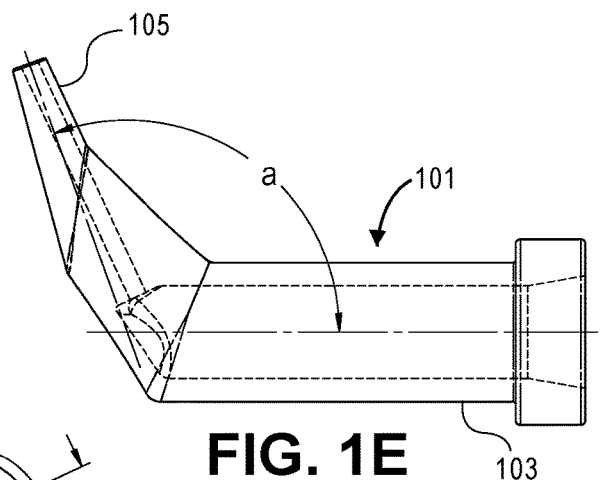
FIG. 1E
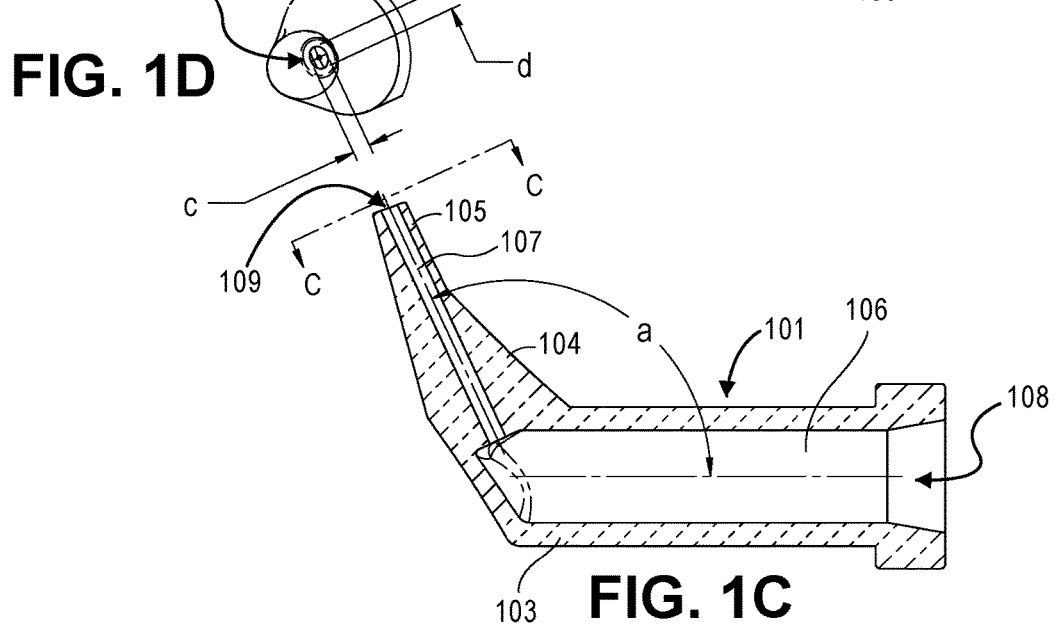
FIG. 1D
FIG. 1C

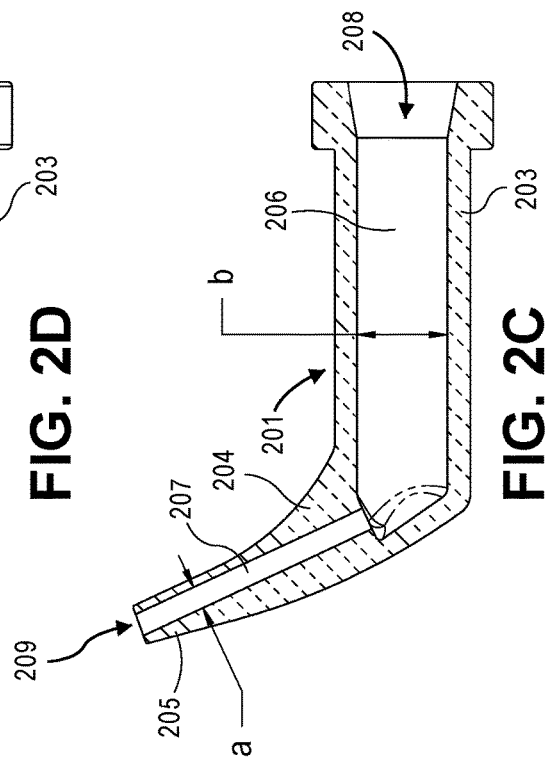
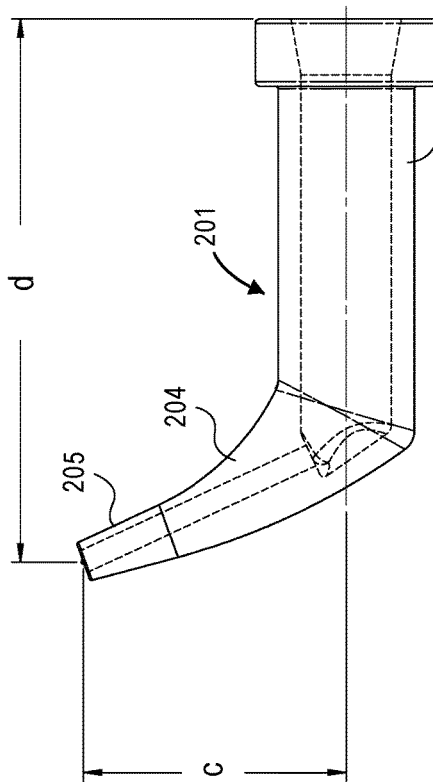
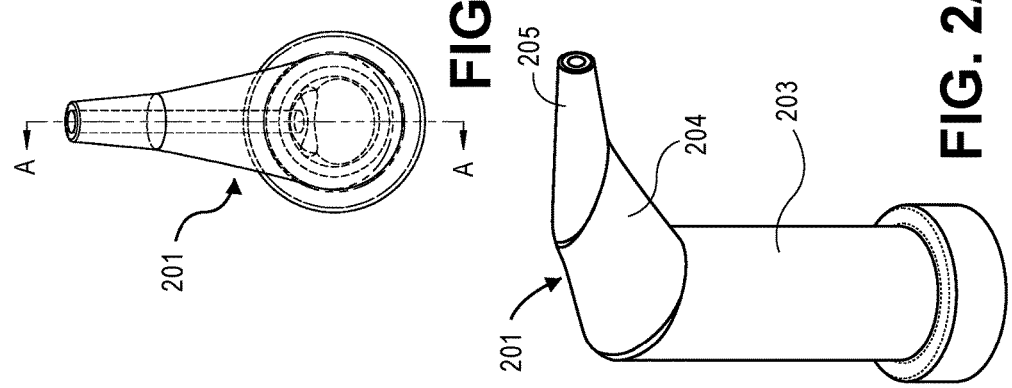
FIG. 2D
FIG. 2C
FIG. 2B
FIG. 2A

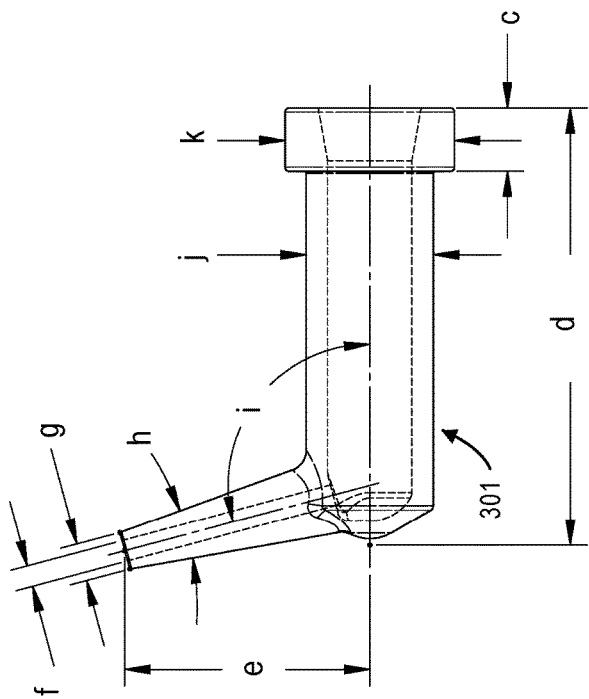
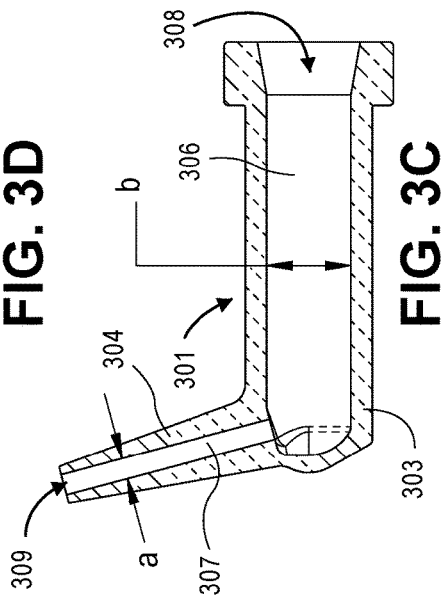
FIG. 3D
FIG. 3C
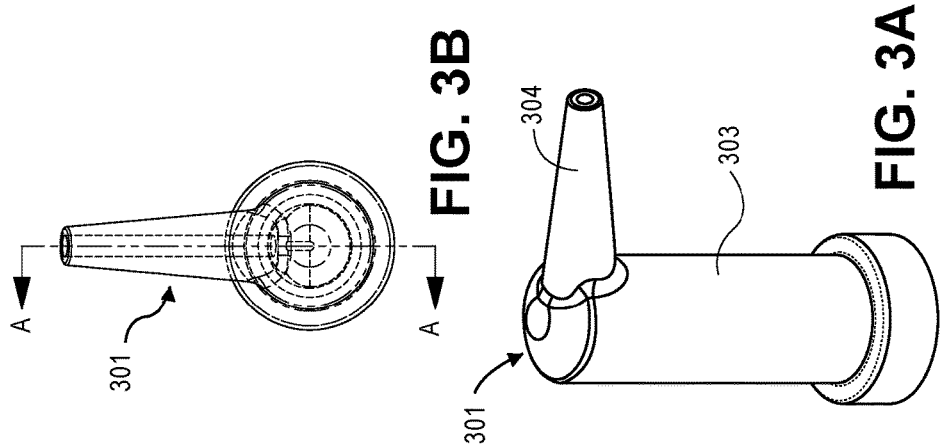
FIG. 3B
FIG. 3A

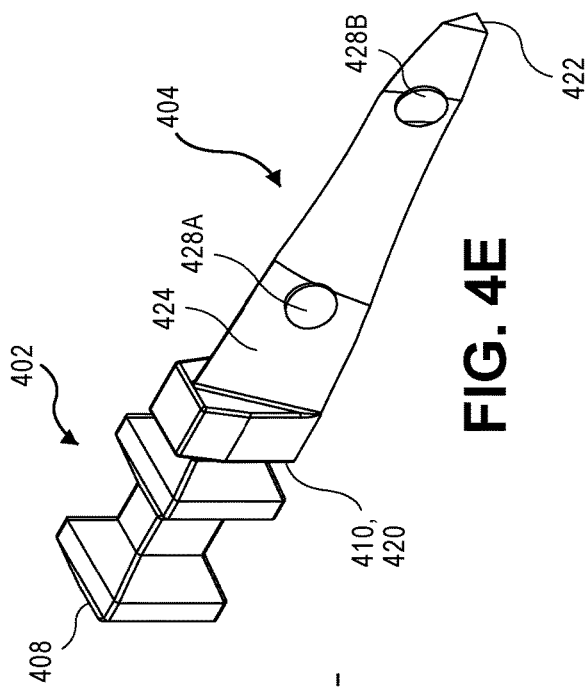
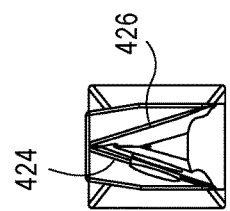
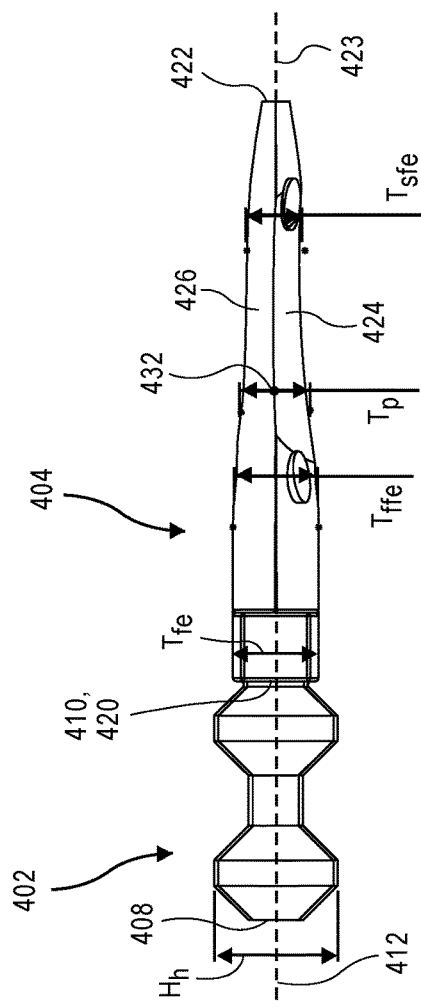
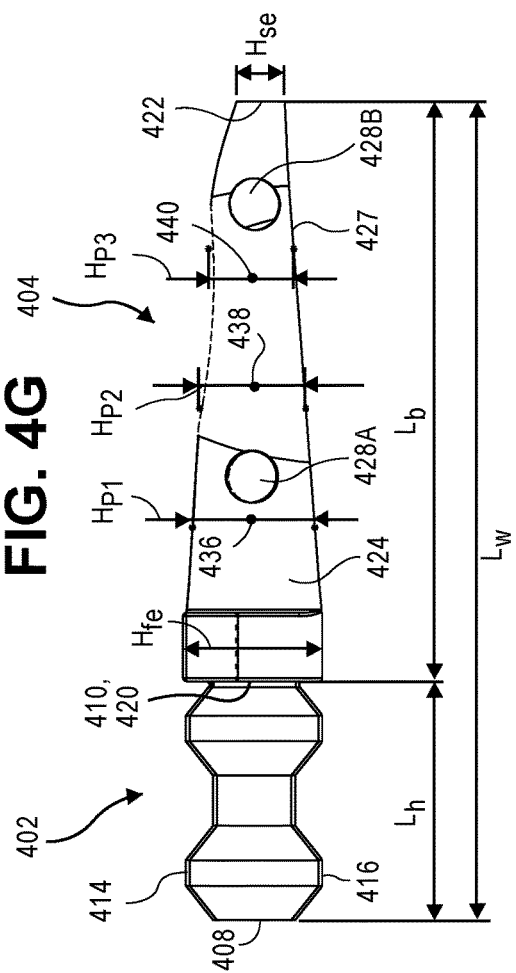

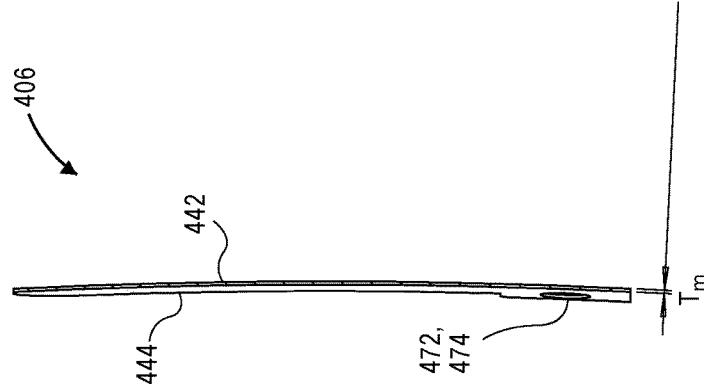
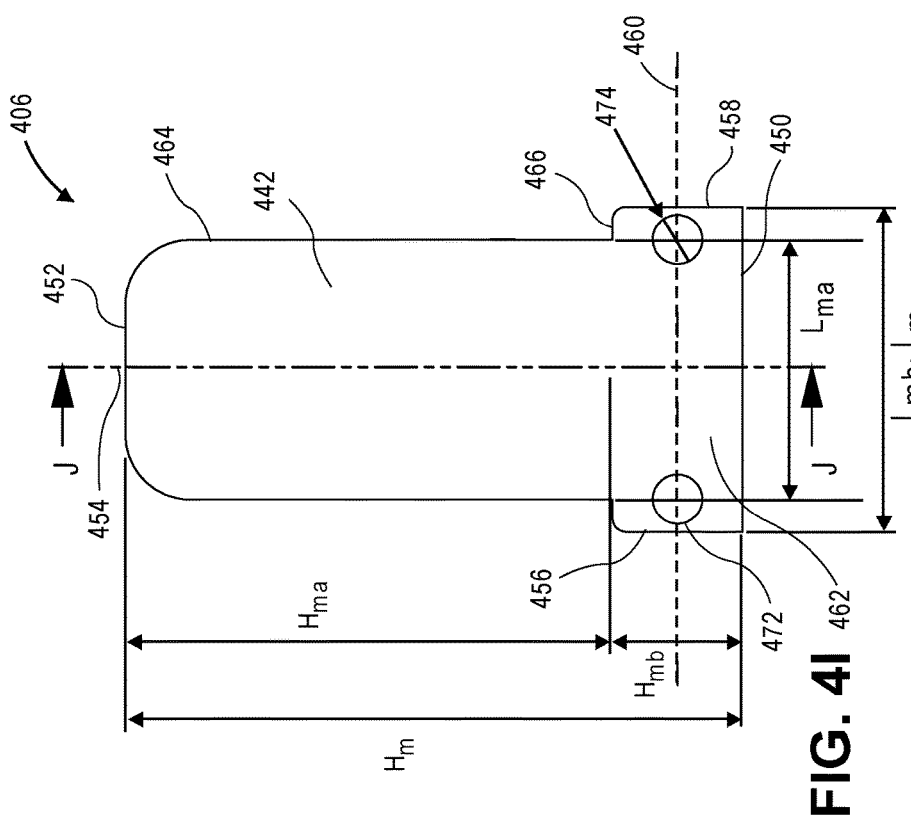
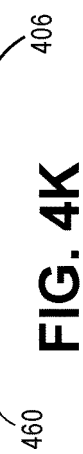

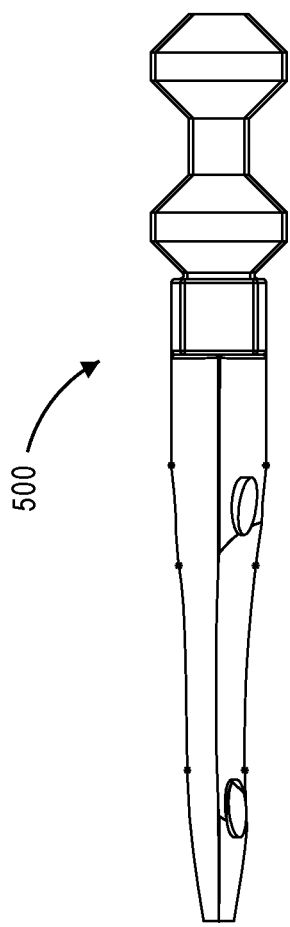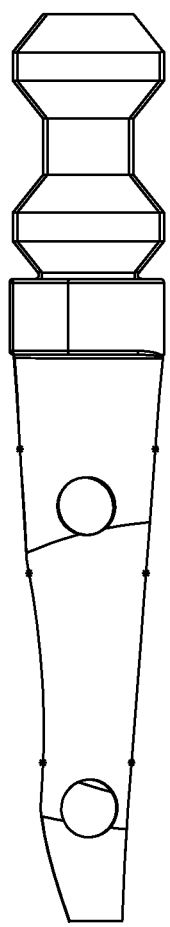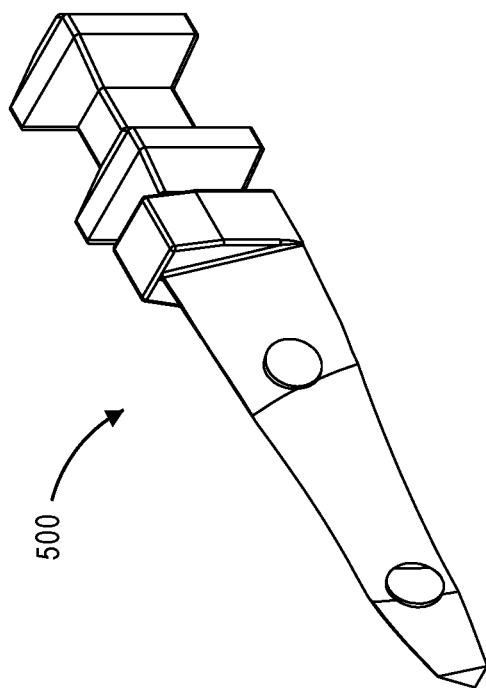
FIG. 5B
FIG. 5C
FIG. 5A

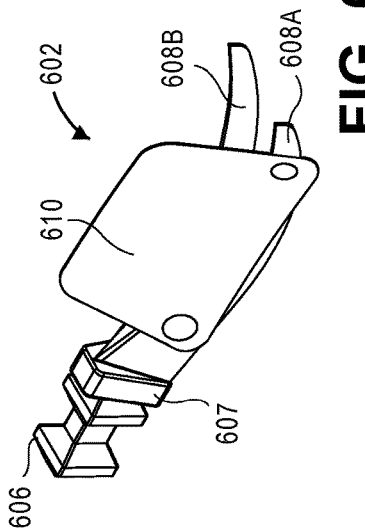
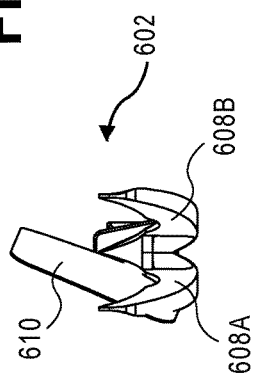
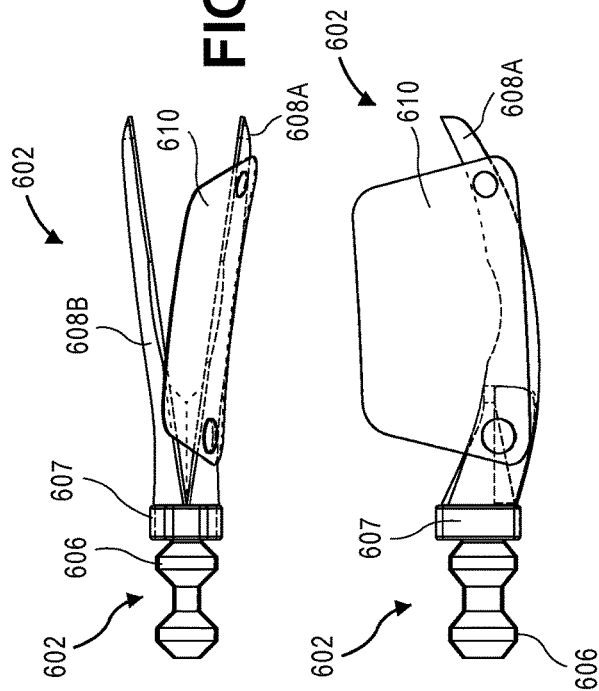
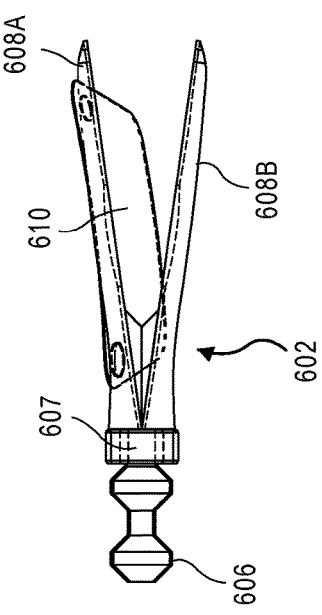

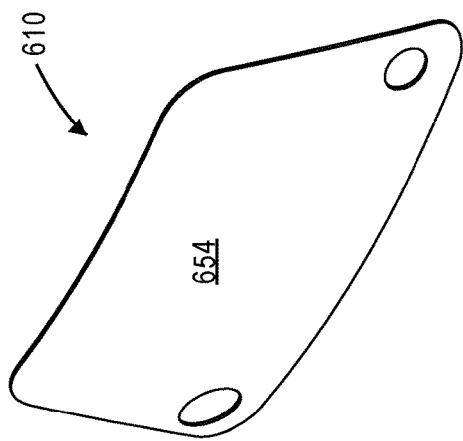
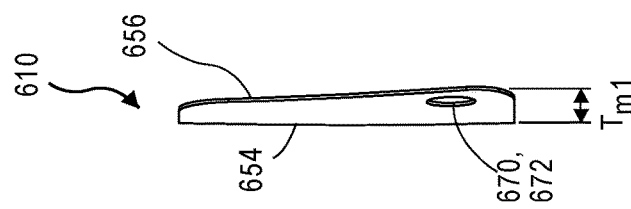
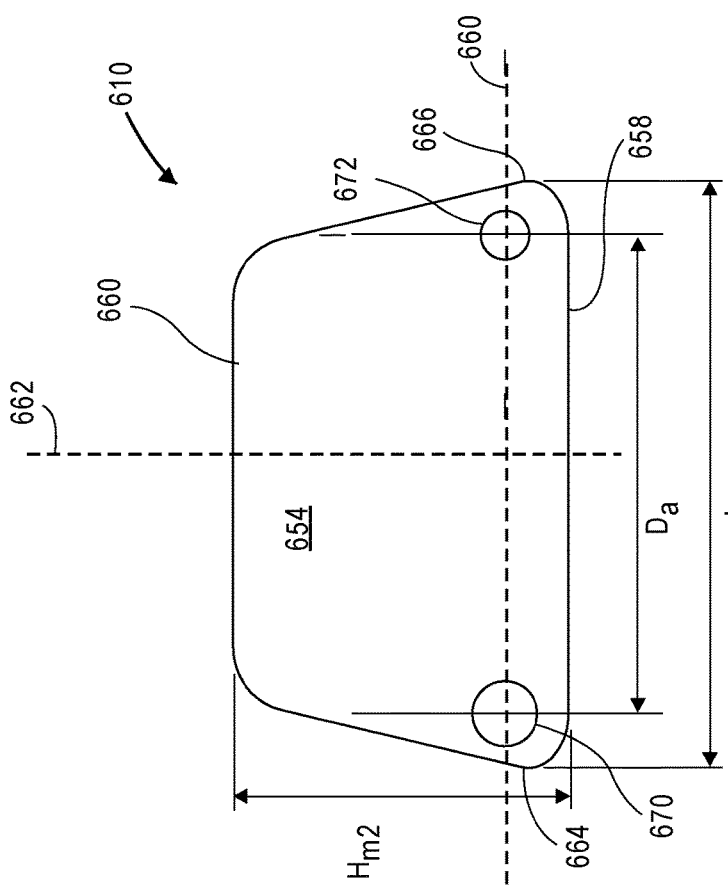
FIG. 6J
FIG. 6L
FIG. 6K
FIG. 6M

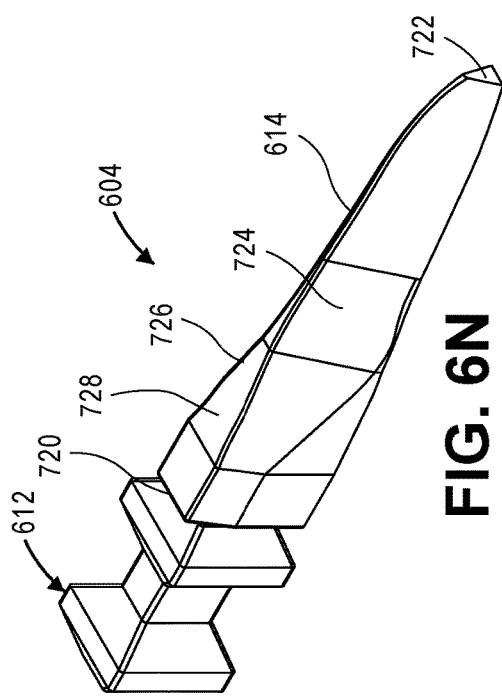
FIG. 6N
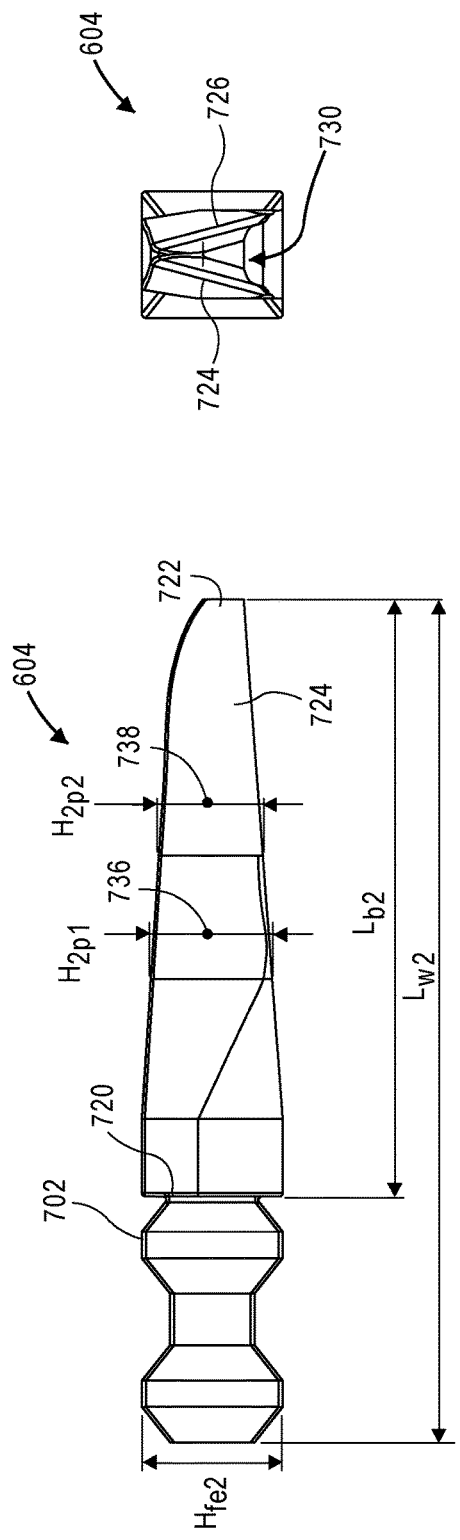
FIG. 6Q
FIG. 6P
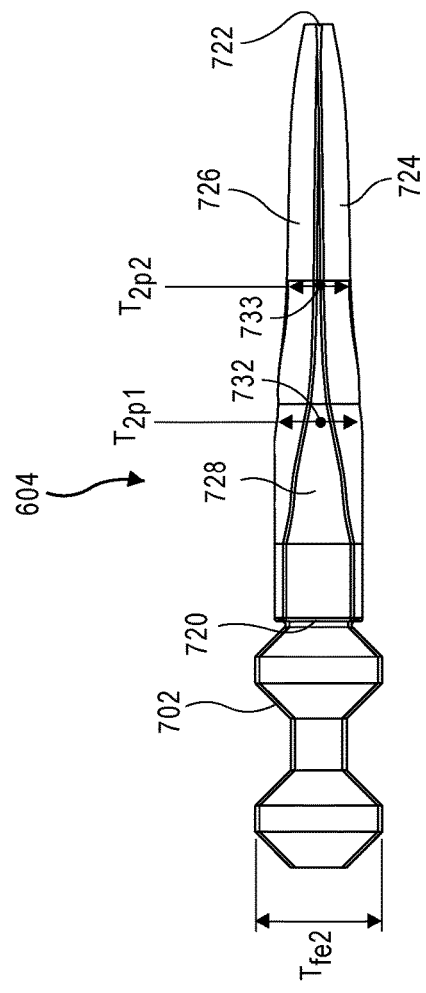
FIG. 6O

DENTAL WEDGES AND MATRIX BANDS FOR USE IN DIRECT COMPOSITE RESTORATION TECHNIQUES FOR POSTERIOR TEETH

CROSS-REFERENCE TO OTHER APPLICATIONS

This application claims benefit of the filing dates of U.S. Provisional Patent Application No. 62/405,099, filed Oct. 6, 2016 and titled "PRODUCTS FOR USE IN DENTAL RESTORATION PROCEDURES," U.S. Provisional Patent Application No. 62/427,669, filed Nov. 29, 2016 and titled "PRODUCTS FOR USE IN DENTAL RESTORATION PROCEDURES," U.S. Provisional Patent Application No. 62/434,229, filed Dec. 14, 2016 and titled "PRODUCTS FOR USE IN DENTAL RESTORATION PROCEDURES," and U.S. Provisional Patent Application No. 62/462,712, filed Feb. 23, 2017 and titled "DENTAL WEDGES AND MATRIX BANDS FOR USE IN COMPOSITING TECHNIQUES," the disclosures of which are hereby incorporated by reference in their entireties.

FIELD

The present disclosure is directed to devices and systems for use in dental restoration procedures. More particularly, the present disclosure is directed to an improved dental wedges and matrix bands, or a unique merging of these two components for use in restoring portions of anterior and posterior teeth.

BACKGROUND

Dentists frequently administer dental restorations to their human patients, such as when human patients have cavities or other conditions that require tooth restoration. Any tooth of a human patient, regardless of mouth position, is susceptible to decay or other conditions that may necessitate a restoration. Human patients have two types of teeth: anterior teeth which include incisors and canine teeth, and posterior teeth which include premolars and molars, and a given patient may need a restoration procedure for any of his/her anterior and/or posterior teeth.

Typically, restoration procedures involve the use of dental composite resins which include various types of synthetic resins that may be composed of Bis-GMA and/or other dimetracrylate monomers (e.g., TEGMA, UDMA, HDDMA), a filler material, and a photoinitiator. To administer a restoration procedure, a dentist typically uses various products or instruments including matrix systems, which consist of metal or plastic matrices, wedges, and 0.2-0.3 g unit dose compules filled with a composite resin that may be dispensed using a dispensing gun.

It is well known that anterior teeth have shapes, sizes (e.g., heights, radii), and contours that are different from those of posterior teeth. It is also well known that the location, size, and shapes of the decayed surfaces that require restoration differ between anterior and posterior teeth. These differences among the tooth types necessitate the presence of two separate systems and methods to restore them.

Thus, existing products and instruments that are used to facilitate restoration of posterior teeth cannot also be used to facilitate restoration of anterior teeth (and vice-versa). U.S. Pat. No. 9,149,343 ("the '343 Patent") discloses an example of such an instrument that is specific in its design to restore posterior teeth. The instrument disclosed therein has a curved wedge body and a matrix that is fixed to the wedge body. The wedge body has a bow shape that completely bends the x-axis (or length axis), and the matrix has a first bow shape along the x-axis and a second bow shape along the y-axis (perpendicular to the x-axis). The wedge body and the matrix band are thus shaped to wrap around the radius of a posterior tooth to be restored in a manner that properly seals the cavitation during the restoration process, which in turn reduces excess resin material, thereby reducing finishing time and preventing the negative consequences (e.g., stains, accumulation of excess plaque) associated with excess resin material, which not only causes early restoration failure but may also lead to gingival inflammation. However, while this said posterior instrument is well-suited for facilitating the restoration of posterior teeth, the instrument cannot be used to facilitate satisfactory restoration of anterior teeth. Because of the instrument's entirely bow shaped x-axis, the wedge body and the matrix will not be properly positioned relative to an anterior tooth (to be restored), which is narrower, has a less convex contour, and has a smaller radius than posterior teeth. Additionally, the shape, size, and contour of the metal matrix band fixed to the wedge are not suitable to produce a valid restoration in the anterior region. This is due to the differently shaped contact points between anterior and posterior teeth. Posterior teeth contact one another in a shape that resembles an oval, with the long portion in the x-axis and the shorter portion in the y-axis. Anterior teeth, with their different shapes and orientation in the oral cavity, have contacts that resemble an oval, but perpendicular to those of posterior teeth, where the long portion lies in the y-axis and the shorter portion lies in the x-axis. As such, the wedge body and the matrix from this posterior-focused system will not create the necessary contact points between the anterior tooth to be restored and a tooth adjacent thereto, and would instead only produce excess resin material associated with the negative consequences described above, and create an unconscionable amount of finishing and refinement necessary to create a restoration falling within the standards of care.

Moreover, existing products and instruments that are used in restoration procedures are generally designed and equipped to facilitate restoration of posterior teeth, as patients are generally more prone to needing restoration to their posterior teeth. Additionally, some existing products that are used in restoration procedures to both posterior and anterior teeth have shortcomings. Further, designs of existing posterior matrix systems have shortcomings.

Accordingly, there is an opportunity for advanced products and instruments, including dental wedges and matrix bands, that are better designed and more suited for restoration procedures to both posterior and anterior teeth.

SUMMARY

In accordance with a first exemplary aspect of the present invention, a wedge system is provided for use in a dental restoration procedure for a posterior tooth. The wedge system includes a first wedge including a body, a first arm extending from the body, a second arm extending from the body, and a gap formed between the first arm and the second arm.

In accordance with a second exemplary aspect of the present invention, a wedge system is provided for use in a dental restoration procedure for a posterior tooth. The wedge system includes a first wedge and a second wedge. The first wedge includes a body, a first arm extending from the body, a second arm extending from the body, and a gap formed between the first arm and the second arm. The second wedge includes a body and an arm extending from the body, wherein at least a portion of the arm of the second wedge is arranged to be disposed in the gap of the first wedge to removably secure the second wedge to the first wedge.

In accordance with a third exemplary aspect of the present invention, a method of preparing a posterior tooth for a dental restoration procedure is provided. The method includes providing a first wedge including a body, a first arm extending from the body, a second arm extending from the body, and a gap formed between the first arm and the second arm. The method also includes inserting the first wedge into an approximal space between the posterior tooth and a tooth adjacent to the posterior tooth.

In further accordance with the foregoing first, second, and/or third aspects, a wedge system and/or method may further include any one or more of the following preferred forms.

In accordance with one preferred form, the first arm extends from the body along a first axis and the second arm extends from the body along a second axis that is angled relative to the first axis.

In accordance with another preferred form, the first wedge further includes a handle extending outward from the body.

In accordance with another preferred form, the wedge system includes a second wedge including a body and an arm extending from the body. At least a portion of the arm of the second wedge is arranged to be disposed in the gap of the first wedge to removably secure the second wedge to the first wedge. When the arm of the second wedge is disposed in the gap of the first wedge, the arm of the second wedge may force the first and second arms of the first wedge away from one another. The second wedge may have an angled bottom surface arranged to facilitate insertion of the second wedge into an approximal space between the posterior tooth and a tooth adjacent the posterior tooth.

In accordance with another preferred form, the wedge system includes a matrix band coupled to and extending outward from the first arm or the second arm of the first wedge. A cutout may be arranged in the first arm to improve adaptation of the matrix band wedge unit to the posterior tooth.

In accordance with another preferred form, the wedge system includes a wing connecting the first arm and the second arm.

In accordance with another preferred form, a second wedge including a body and an arm extending from the body is provided. After the first wedge is inserted into the approximal space, the second wedge may be inserted into the approximal space such at least a portion of the arm of the second wedge is disposed in the gap of the first wedge, thereby removably securing the second wedge to the first wedge.

In accordance with another preferred form, disposing at least the portion of the arm of the second wedge in the gap of the first wedge may include driving the first arm of the first wedge toward the posterior tooth and driving the second arm of the first wedge away from the first arm and toward the tooth adjacent the posterior tooth.

BRIEF DESCRIPTION OF THE FIGURES

FIG. 1C is a section view of the compule of FIG. 1A.
FIG. 1D is a detailed view of a section of the compule of FIG. 1A.
FIG. 1E is a side view of the compule of FIG. 1A.
FIG. 2A depicts a perspective view of an example compule that can be used in a dental restoration procedure.
FIG. 2B is a top view of the compule of FIG. 2A.
FIG. 2C is a section view of the compule of FIG. 2A.
FIG. 2D is a side view of the compule of FIG. 2A.
FIG. 3A depicts a perspective view of an example compule that can be used in a dental restoration procedure.
FIG. 3B is a top view of the compule of FIG. 3A.
FIG. 3C is a section view of the compule of FIG. 3A.
FIG. 3D is a side view of the compule of FIG. 3A.
FIG. 4E is a perspective view of a body portion and a handle portion of the wedge of FIG. 4A;
FIG. 4F is a front view of FIG. 4E.
FIG. 4G is a top view of FIG. 4E.
FIG. 4H is an end view of FIG. 4E.
FIG. 4I is a front view of a matrix band of the wedge of FIG. 4A.
FIG. 4J is a cross-sectional view taken along line J-J in FIG. 4I.
FIG. 4K is a top view of FIG. 4I.
FIG. 5A depicts a perspective view of another example of a wedge that can be used in a dental restoration procedure for an anterior tooth.
FIG. 5B is a top view of the wedge of FIG. 5A.
FIG. 5C is a front view of the wedge of FIG. 5A.
FIG. 6A depicts a perspective view of one example of a wedge that can be used in a dental restoration procedure for a posterior tooth.
FIG. 6B is a top view of the wedge of FIG. 6A.
FIG. 6C is a front view of the wedge of FIG. 6A.
FIG. 6D is a bottom view of the wedge of FIG. 6A.
FIG. 6E is an end view of the wedge of FIG. 6A.
FIG. 6J is a perspective view of a matrix band of the wedge of FIG. 6A.
FIG. 6K is a front view of the matrix band of FIG. 6J.
FIG. 6L is a side view of the matrix band of FIG. 6J.
FIG. 6M is a top view of the matrix band of FIG. 6J.

FIG. 6N depicts a perspective view of one example of a wedge that can be used in combination with the wedge of FIG. 6A in a dental restoration procedure for a posterior tooth.

FIG. 6O is a front view of the wedge of FIG. 6N.

FIG. 6P is a top view of the wedge of FIG. 6N.

FIG. 6Q is an end view of the wedge of FIG. 6N.

DETAILED DESCRIPTION

The present disclosure provides improved compules, wedges, matrix bands, and wedge systems that may be used in dental restoration procedures.

FIGS. 1A-1G, 2A-2D, and 3A-3E depict various views of various designs of example compules having different shapes and sizes, where the compules may be used in restoration procedures to anterior and posterior teeth. Generally, the compules may be one solid unit or multiple connected portions. The compules may be composed of various metallic or plastic materials, or combinations thereof. Additionally, the compules may be configured to receive and retain a composite material to be used in dental restoration procedures, such as any hybrid or nano composite material. It should be appreciated that the values and parameters for the dimensions of the compules as described herein are merely examples, and that alternative dimensions and parameters, or ranges of dimensions and parameters, are envisioned.

Figure 1A:
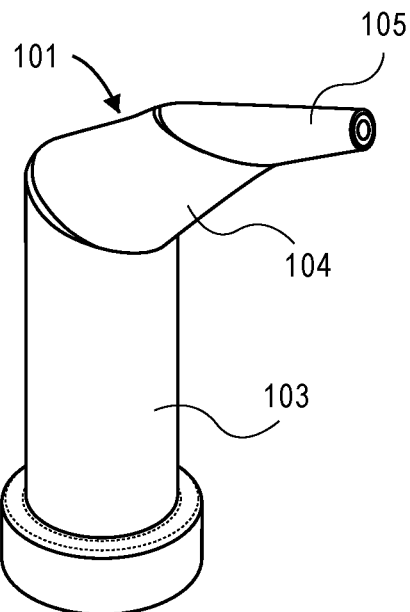
FIG. 1A depicts a perspective view of an example compule that can be used in a dental restoration procedure.

FIGS. 1A-1G depict various views of a compule 101 having a segmented nozzle. FIG. 1A depicts a perspective view of the compule 101, where the compule 101 may include an angled end or arm that includes two (2) distinct segments that extend at different angles from a main body portion 103. Generally, a secondary body portion 104 may extend from the main body portion 103 at a first angle, and a tertiary body portion 105 may extend from the secondary body portion 104 at a second angle relative to the main body portion 103.

Figure 1B:
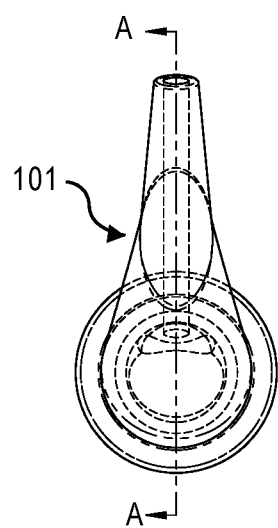
FIG. 1B is a top view of the compule of FIG. 1A.

FIG. 1B depicts a top view of the compule 101, where FIG. 1B depicts a section line "A" that corresponds to a section view of the compule 101 illustrated in FIG. 1C. As illustrated in FIG. 1C, the main body portion 103 of the compule 101 may include a main cavity 106 that extends therethrough, from an opening 108 to about where the secondary body portion 104 connects to the main body portion 103. The main cavity 106 may connect to a secondary cavity 107 that extends through the secondary body portion 104 and the tertiary body portion 105, where the secondary cavity 107 may extend from the main cavity 106 through an opening 109 or tip of the tertiary body portion 105. In use, a composite material may be loaded into the opening 108, where the cavities 106, 107 may direct the composite material through the compule 101 so that the composite material may exit the compule 101 through the opening 109.

FIG. 1C depicts a section line "C" that corresponds to a view of a tip 102 and the opening 109 of the compule 101 illustrated in FIG. 1D. The opening 109 may be circle-shaped or oval-shaped and may have two dimensions having various values: a "c" diameter and a "d" diameter. According to some embodiments, the "c" diameter may have a value ranging from 0.60-1.40 mm; and the "d" diameter may have a value ranging from 0.85-1.65 mm.

FIG. 1E illustrates a side view of the compule 101, where the main body portion 103 and the tertiary body portion 105 may have an angle "a" therebetween. In an embodiment, the angle "a" may be approximately 110 degrees, however alternative angles are envisioned (e.g., any angle between 90 and 130 degrees).

Figure 1G:
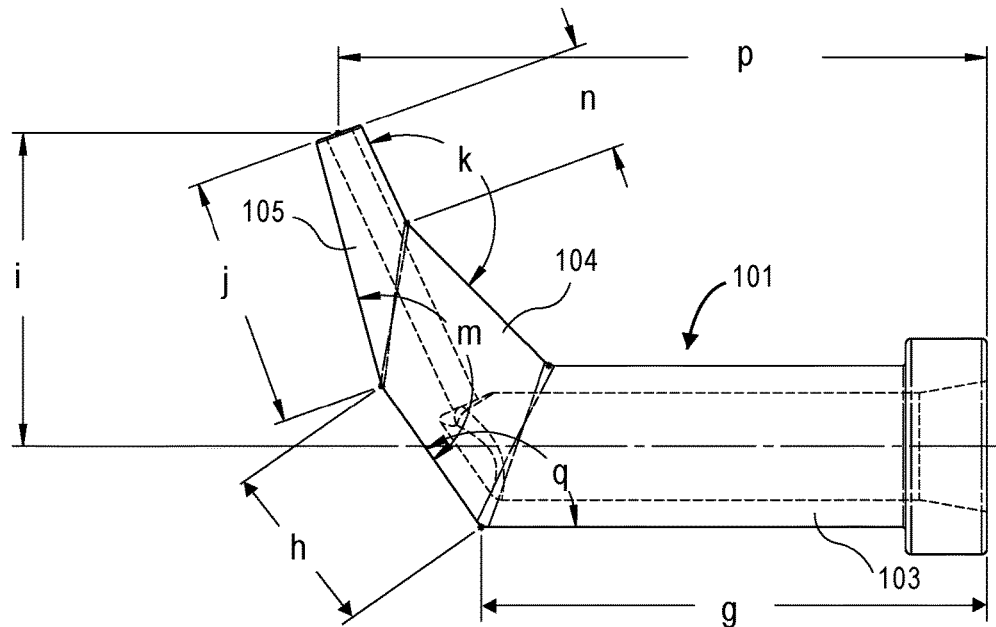
FIG. 1G is a side view of the compule of FIG. 1A.
Figure 1F:
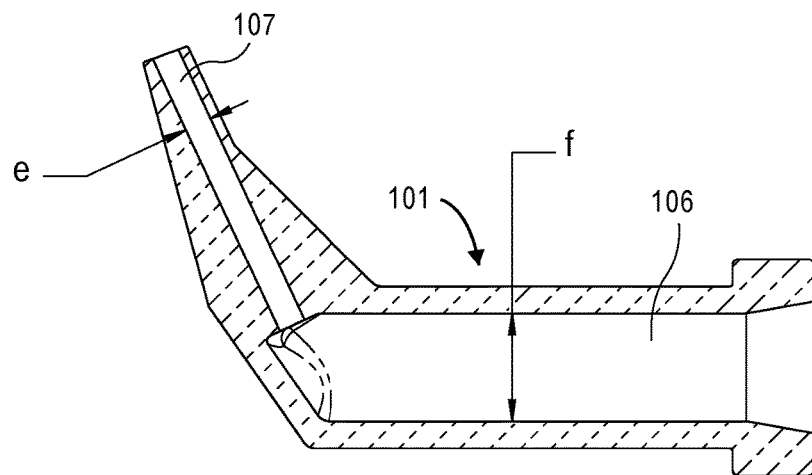
FIG. 1F is a section view of the compule of FIG. 1A.

FIG. 1F illustrates a cross-section view of the compule 101 and the cavities 106, 107, where the cavity 106 may have a width dimension "f" and the cavity 107 may have a width dimension "e". In an embodiment, the width dimension "f" may be approximately 4.0 mm, however alternative dimensions are envisioned (e.g., any dimension between 3.0 and 5.0 mm); and the width dimension "e" may be approximately 1.0 mm, however alternative dimensions are envisioned (e.g., any dimension between 0.5 and 2.0 mm).

FIG. 1G depicts a side view of the compule 101. As illustrated in FIG. 1G, the compule 101 and its body portions 103, 104, 105 may have dimensions "g", "h", "i", "j", "k", "m", "n", "p", and "q" having various values. In particular, the dimension "g" may range from 17.0-21.0 mm; the dimension "h" may range from 5.5-7.5 mm; the dimension "i" may range from 10.5-12.5 mm; the dimension "j" may range from 8.5-10.5 mm; the dimension "k" may range from 145-175 degrees; the dimension "m" may range from 145-175 degrees; the dimension "n" may range from 3.0-5.0 mm; the dimension "p" may range from 22.0-26.0 mm; and the dimension "q" may range from 110-140 degrees.

FIGS. 2A-2D depict various views of another compule 201 having a segmented nozzle. FIG. 2A depicts a perspective view of the compule 201, where the compule 201 may include an angled end or arm that includes two (2) distinct segments that extend at different angles from a main body portion 203. Generally, a secondary body portion 204 may extend from the main body portion 203 at a first angle, and a tertiary body portion 205 may extend from the secondary body portion 204 at a second angle relative to the main body portion 203.

FIG. 2B depicts a top view of the compule 201, where FIG. 2B depicts a section line "A" that corresponds to a section view of the compule 201 illustrated in FIG. 2C. As illustrated in FIG. 2C, the main body portion 203 of the compule 201 may include a main cavity 206 that extends therethrough, from an opening 208 to about where the secondary body portion 204 connects to the main body portion 203. The main cavity 206 may connect to a secondary cavity 207 that extends through the secondary body portion 204 and the tertiary body portion 205, where the secondary cavity 207 may extend from the main cavity 206 through an opening 209 or tip of the tertiary body portion 205. In use, a composite material may be loaded into the opening 208, where the cavities 206, 207 may direct the composite material through the compule 201 so that the composite material may exit the compule 201 through the opening 209.

The opening 209 may be circle-shaped and may have a diameter "a" that corresponds to the width of the secondary cavity 207. According to embodiments, the diameter "a" may range from 0.75-1.75 mm. Similarly, the main cavity 206 may have a width "b" that may range from 3.0-5.0 mm. In embodiments, the opening 209 may be oval-shaped, in which case the opening 209 may have two different diameter dimensions. For example, a first diameter dimension may range from 0.75-1.75 mm and a second diameter dimension may range from 0.50-1.50 mm.

FIG. 2D depicts a side view of the compule 201. As illustrated in FIG. 2D, the compule 201 and its body portions 203, 204, 205 may have dimensions "c" and "d" having various values. In particular, the dimension "c" may range from 10.0-13.0 mm, and the dimension "d" may range from 22.0-26.0 mm.

Figure 3E:
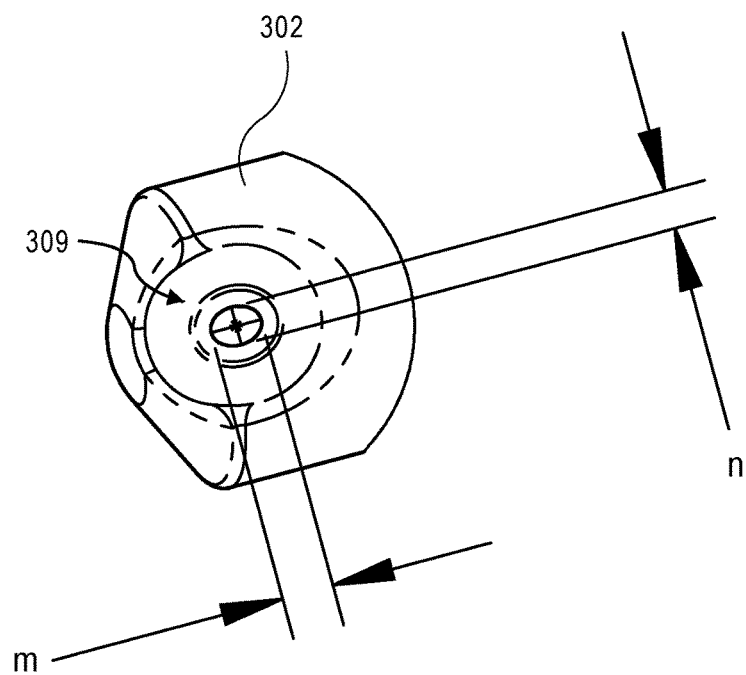
FIG. 3E is a detailed view of a section of the compule of FIG. 3A.

FIGS. 3A-3E depict various views of a compule 301 having a segmented nozzle. FIG. 3A depicts a perspective view of the compule 301, where the compule 301 may include a secondary body portion 304 that extends at an angle from a main body portion 303.

FIG. 3B depicts a top view of the compule 301, where FIG. 3B depicts a section line "A" that corresponds to a section view of the compule 301 illustrated in FIG. 3C. As illustrated in FIG. 3C, the main body portion 303 of the compule 301 may include a main cavity 306 that extends therethrough, from an opening 308 to about where the secondary body portion 304 connects to the main body portion 303. The main cavity 306 may connect to a secondary cavity 307 that extends through the secondary body portion 304, where the secondary cavity 307 may extend from the main cavity 306 through an opening 309 or tip of the secondary body portion 304. In use, a composite material may be loaded into the opening 308, where the cavities 306, 307 may direct the composite material through the compule 301 so that the composite material may exit the compule 301 through the opening 309.

FIG. 3C further indicates a width dimension "a" of the cavity 307 and a width dimension "b" of the cavity 306. In an embodiment, the width dimension "b" may be approximately 4.0 mm, however alternative dimensions are envisioned (e.g., any dimension between 3.0 and 5.0 mm); and the width dimension "a" may be approximately 1.0 mm, however alternative dimensions are envisioned (e.g., any dimension between 0.5 and 2.0 mm).

FIG. 3D depicts a side view of the compule 301. As illustrated in FIG. 3D, the compule 301 and its body portions 303, 304 may have dimensions "c", "d", "e", "f", "g", "h", "i", "j", and "k" having various values. In particular, the dimension "c" may range from 2.0-4.0 mm; the dimension "d" may range from 19.0-23.0 mm; the dimension "e" may range from 9.5-13.5 mm; the dimension "f" may range from 0.75-2.0 mm; the dimension "g" may range from 1.5-2.5 mm; the dimension "h" may be an angle associated with the secondary body portion 304, and may range from 5-20 degrees; the dimension "i" may be an angle between the main body portion 303 and the secondary body portion 304, and may range from 95-120 degrees; the dimension "j" may range from 4.5-7.5 mm; and the dimension "k" may range from 6.0-10.0 mm.

FIG. 3E depicts a view of a tip 302 and the opening 309 of the compule 301. The opening 309 may be circle-shaped or oval-shaped and may have two dimensions having various values: an "m" diameter and an "n" diameter. According to some embodiments, the "m" diameter may have a value ranging from 1.0-2.0 mm; and the "n" diameter may have a value ranging from 0.75-1.5 mm.

FIGS. 4A-4K depict one example of a wedge 400 that is specifically designed for use in a dental restoration procedure for an anterior tooth. More particularly, the wedge 400 is adapted to be disposed in an approximal space between the anterior tooth to be restored and a tooth adjacent the anterior tooth (the adjacent tooth may also be an anterior tooth). The wedge 400 generally includes a handle portion 402, a body portion 404 that is coupled to (e.g., integrally formed with) and extends outward from the handle portion 402, and a matrix band 406 coupled to the body portion 404.

As will be described in greater detail below, when the wedge 400 is disposed in the approximal space, the body portion 404 and the matrix band 406 intimately contact the anterior tooth to be repaired in a manner that seals a cavity of the anterior tooth while substantially approximating the adjacent tooth. Thus, the body portion 404 and the matrix band 406 not only reduce, if not prevent, excess material, thereby reducing finishing time and reducing the failure rate of the dental restoration procedure, but also facilitate the creation of contact points between the anterior tooth and the adjacent tooth, which are desired.

The handle portion 402 generally allows a dentist to grasp the wedge 400 for the purpose of positioning the wedge 400 in or removing the wedge 400 from the approximal space. The handle portion 402 may have the shape illustrated in FIGS. 4A-4F, or may have any other suitable shape. The handle portion 402 extends from a first end 408 to a second end 410 along a handle axis 412. In other words, the handle portion 402 has a length $L_h$ defined between the first end 408 and the second end 410. In this example, the length $L_h$ is equal to approximately 3.5 mm. In other examples, however, the length $L_h$ can be greater than or less than 3.5 mm. The handle portion 402 also has a height $H_h$ defined between a top side 414 and a bottom side 416 (i.e., perpendicular to the handle axis 412). In this example, the height $H_h$ is equal to approximately 2 mm, though in other examples, the height $H_h$ can be greater than or less than 2 mm.

The body portion 404 is generally configured to substantially fill the approximal space between the anterior tooth and the adjacent tooth and position the matrix band 406 in the desired position. As best illustrated in FIG. 4G, the body portion 404 in this example extends from a first end 420, positioned immediately adjacent the handle portion 402, to a second end 422, remote from the handle portion 402, along a body axis 423 that is parallel to and co-axial with the handle axis 412. In other words, the body portion 404 is linear (or substantially linear). As best illustrated in FIGS. 4E-4F, the body portion 404 in this example has a substantially triangular shape defined by a substantially triangular front surface 424, a substantially triangular rear surface 426 opposite the front surface 424, and a substantially triangular bottom surface 427 that connects the front and rear surfaces 424, 426. It will be appreciated that the front surface 424, which is partially curved and partially flat, will face the anterior tooth to be restored, and the rear surface 426, which is substantially flat, will face the adjacent tooth when the body portion 404 is disposed in the approximal space.

The body portion 404 also includes first and second fastening elements 428A, 428B that securely retain the matrix band 406 thereon. In this example, the fastening elements 428A, 428B each take the form of a circular projection that extends outward from the front surface 424. In other examples, however, the body portion 404 may only include one fastening element, may include more than two fastening elements, or may include none at all (e.g., the body portion 404 may instead include one or more apertures sized to receive one or more fasteners to secure the matrix band 406 to the body portion 404).

As best illustrated in FIG. 4F, the body portion 404 has a length $L_b$ defined between the first end 420 and the second end 422 and along the body axis 423. In this example, the length $L_b$ is equal to approximately 8.5 mm, such that the total length $L_w$ of the wedge 400 is equal to approximately 12 mm. In other examples, however, the length $L_b$ can be greater than or less than 8.5 mm, with the total length $L_w$ of the wedge 400 being greater than or less than approximately 12 mm (e.g., the total length $L_w$ can be in a range of between 8 mm and 14 mm). In any case, the body portion 404 has a thickness, defined herein as the distance between the front and rear surfaces 424, 426, that decreases, slightly increases, and then further decreases as the body portion 404 extends from the first end 420 to the second end 422. In this example, the thickness $T_{fe}$ at the first end 420 is equal to approximately 1.25 mm, the thickness $T_{ffe}$ at the first fastening element 428A is equal to approximately 1.25 mm, the thickness $T_p$ at a point 432 located between the first and second fastening elements 428A, 428B is equal to approximately 1.01 mm, and the thickness $T_{sfe}$ at the second fastening element 428B is equal to approximately 0.84 mm. In other examples, however, these thickness values may vary. As an example, the thickness $T_{fe}$ may be greater than approximately 1.25 mm but less than approximately 2.5 mm. The body portion 404 also has a height that decreases or tapers as the body portion 404 extends from the first end 420 to the second end 422, such that the bottom of the body portion 404 is angled relative to the horizontal (see FIG. 4F), which may help to position the wedge 400 within the approximal space. In this example, the height $H_{fe}$ at the first end 420 is equal to approximately 2 mm, the height $H_{p1}$ at a first point 436 between the first end 420 and the first fastening element 428A is equal to approximately 1.79 mm, the height $H_{p2}$ at a second point 438 between the first and second elements 428A, 428B is equal to approximately 1.55 mm, the height $H_{p3}$ at a third point 440 between the first and second elements 428A, 428B is equal to approximately 1.17 mm, and the height $H_{se}$ at the second end 422 is equal to approximately 0.70 mm. In other examples, however, these height values may vary. As an example, the height $H_{p1}$ may be any value greater than approximately 1.25 mm and less than 3.0 mm, and the height $H_{p3}$ may be any value greater than approximately 0.75 mm and less than approximately 2.0 mm.

As a result of the foregoing, the body portion 404 has or defines a localized curve. Stated differently, only part of the body portion 404 is curved, with the remainder of the body portion 404 being flat. In this example, the localized curve is defined between the first and second fastening elements 428A, 428B, with the result that the only part of the body portion 404 that is curved is located between the first and second fastening elements 428A, 428B. In other examples, however, the localized curve can be defined between different points along the body portion 404.

As illustrated in FIGS. 4I-4J, the matrix band 406 has a thin profile that is defined by a front surface 442, a rear surface 444 opposite the front surface 442, and a thickness $T_m$ between the front and rear surfaces 442, 444. The front surface 442 is arranged to face (and engage) the anterior tooth to be restored, while the rear surface 444 is arranged to face the tooth adjacent the anterior tooth to be restored, when the wedge 400 is in use. As also illustrated in FIGS. 4I-4J, the matrix band 406 generally extends from a first end 450 to a second end 452 along a height axis 454 and generally extends from a first side 456 to a second side 458 along a length axis 460. As best illustrated in FIG. 4J, the matrix band 406 has a slight, gradual, and smooth concave curvature along and away from the height axis 454. As best illustrated in FIG. 4K, the matrix band 406 has a slight, gradual, and smooth concave curvature along the length axis 460. In this example, the matrix band 406 may have a radius of curvature 21 mm, though in other examples, the radius of curvature can be any value in a range of between 17 mm and 25 mm. Thus, it will be appreciated that portions of the matrix band 406 between the first and second sides 456, 458 are slightly offset from the length axis 460.

The matrix band 406 has a base 462 and an arm 464 that is coupled to (e.g., integrally formed with) and extends outward (upward, in FIG. 4I) from the base 462. The base 462 has a substantially rectangular shape defined by the first end 450, a shoulder 466 that connects the base 462 to the arm 464, and the first and second sides 456, 458, which connect the first end 450 and the shoulder 458. The base 462 thus has a height $H_{mb}$ that is defined between the first end 450 and the shoulder 466, and a length $L_{mb}$ that is defined between the first and second sides 456, 458. The arm 464 also has a substantially rectangular shape defined by the second end 452, the shoulder 466, and the first and second sides 456, 458. The arm 464 thus has a height $H_{ma}$ that is defined between the second end 452 and the shoulder 466, and a length $L_{ma}$ that is defined between the first and second sides 456, 458. As best illustrated in FIG. 4I, the length $L_{mb}$ of the base 462 is greater than the length $L_{ma}$ of the arm 464, such that the length $L_{mb}$ of the base 462 defines the length $L_m$ of the matrix band 406 itself. Meanwhile, the height $H_m$ of the matrix band 406 is defined by the sum of the height $H_{mb}$ of the base 462 and the height $H_{ma}$ of the arm 464.

It will be appreciated from FIG. 4I that the height $H_m$ of the matrix band 406 is greater than the length $L_m$ of the matrix band 406. In other words, the matrix band 406 has a incisal-gingival dimension and a buccal-lingual dimension that is smaller than the incisal-gingival dimension. The height $H_m$ of the matrix band 406 is preferably in a range between approximately 7 mm and approximately 12 mm, while the length $L_m$ of the matrix band 406 is preferably in a range between approximately 3.5 mm and approximately 5.5 mm. Thus, in some examples, the height $H_m$ of the matrix band 406 may be at least twice as large as the length $L_m$ of the matrix band. In this example, the height $H_m$ of the matrix band 406 is 9.5 mm, and the length $L_m$ of the matrix band 406 is 5 mm (with the length $L_{ma}$ of the arm 464 being 4 mm). It will also be appreciated from FIGS. 4I and 4J that the thickness $T_m$ of the matrix band 406 is considerably smaller than the height $H_m$ and the length $L_m$ of the matrix band 406. In this example, the thickness $T_m$ is equal to 0.05 mm, though the thickness $T_m$ can vary between approximately 0.025 mm and approximately 0.05 mm.

With the body portion 404 and the matrix band 406 so dimensioned, the body portion 404 is configured to engage, retain, and support the matrix band 406. More particularly, the localized curvature of the body portion 404 allows the matrix band 406 to maintain a matching curvature. This localized curvature of both the body portion 404 and the matrix band 406 further allows the wedge 400 to engage with the convex surface of the anterior tooth to be restored when inserted into the approximal space. The matrix band 406 is coupled to the body portion 404 so that the rear surface 444 of the matrix band 406 faces, and at least partially contacts, the front surface 424 of the body portion 404. In this example, the matrix band 406 is coupled to the body portion 404 via the first and second fastening elements 428A, 428B, which are received in first and second similarly shaped apertures 472, 474, respectively, formed in the rear surface 444 of the matrix band 406. In this example, the distance between the apertures 472, 474 is approximately equal to the length of the arm 464 of the matrix band 406, though this need not be the case. The fastening elements 428A, 428B may be secured therein in any known manner. In other examples, the matrix band 406 may be coupled to the body portion 404 via one fastening element, more than two fastening elements, or in some other manner. In any case, when the matrix band 406 is coupled to the body portion 404, as shown in FIGS. 4A-4D, the height axis 454 is angled relative to the body axis 423. As an example, the height axis 454 be may oriented at an angle of between 75 degrees and 90 degrees relative to the body axis 423.

Figure 4A:
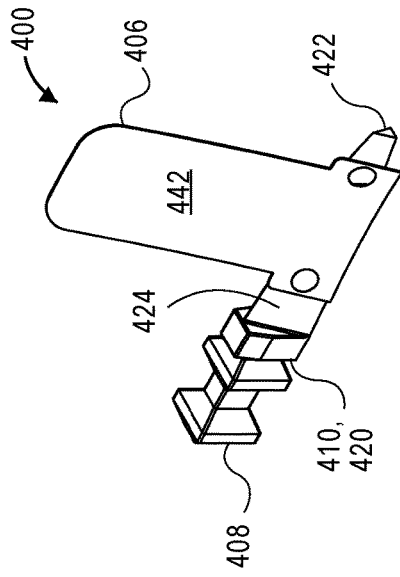
FIG. 4A depicts a perspective view of one example of a wedge that can be used in a dental restoration procedure for an anterior tooth.
Figure 4D:
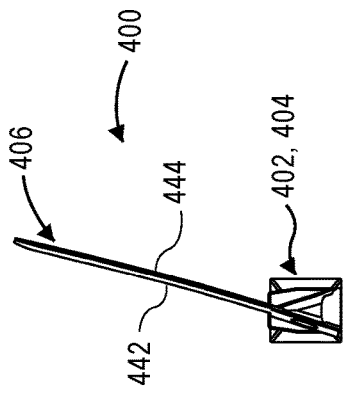
FIG. 4D is an end view of the wedge of FIG. 4A.
Figure 4C:
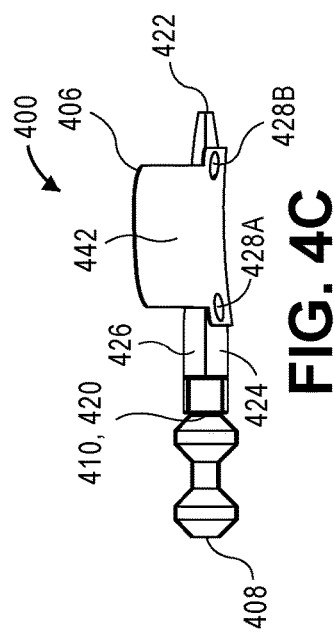
FIG. 4C is a top view of the wedge of FIG. 4A.
Figure 4B:
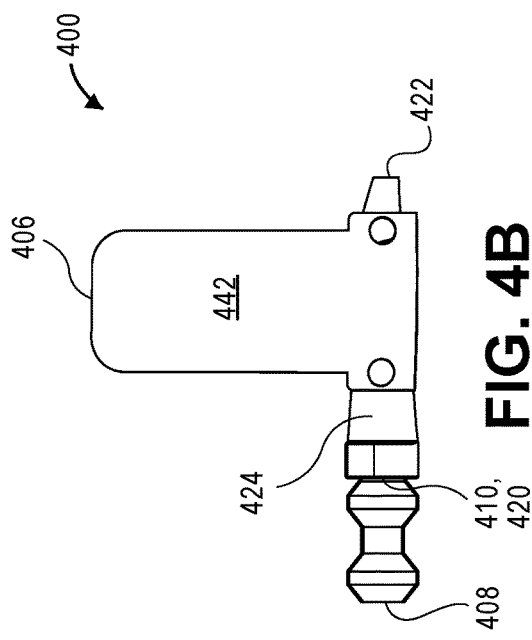
FIG. 4B is a front view of the wedge of FIG. 4A.
Figure 4L:
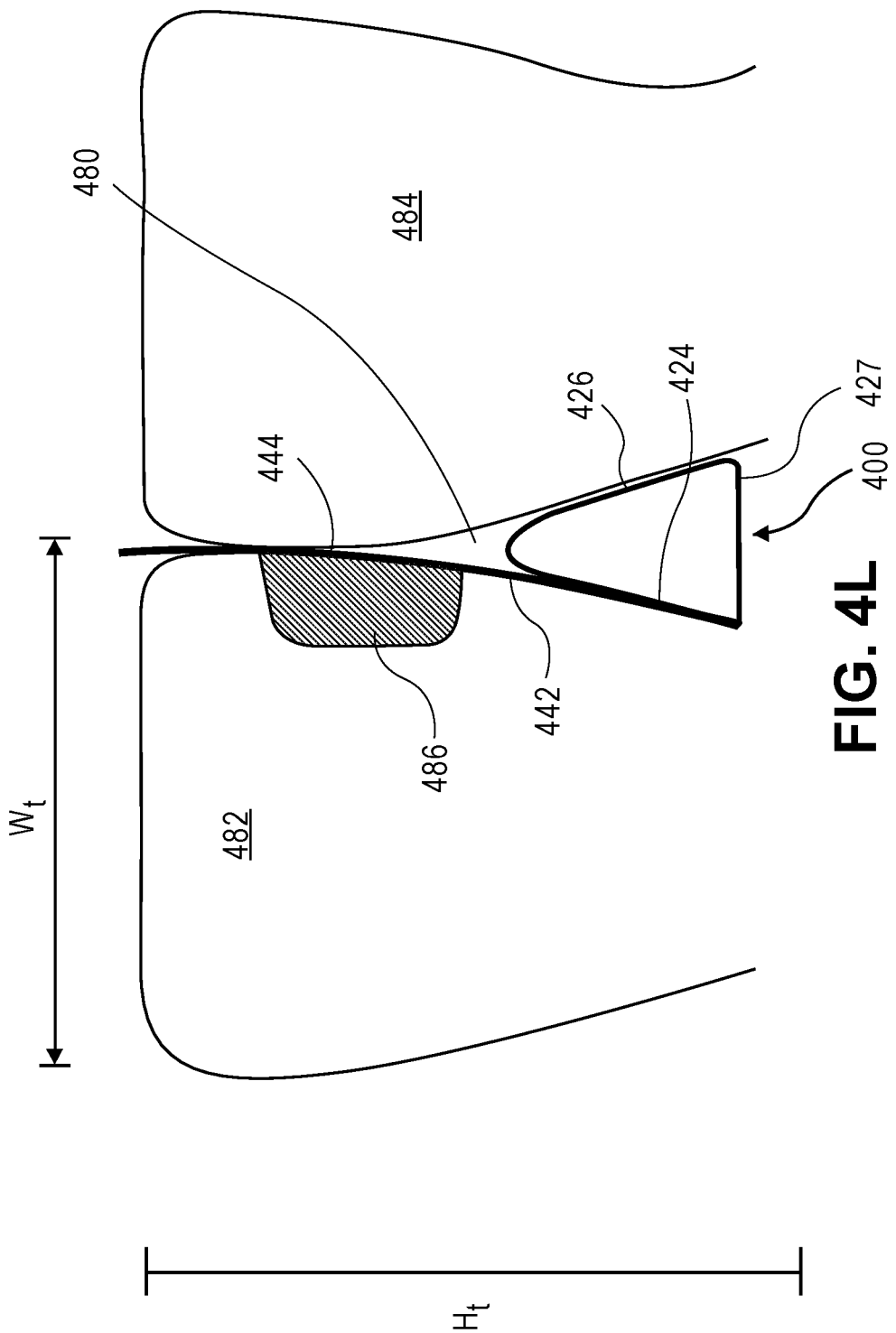
FIG. 4L illustrates the wedge of FIG. 4A positioned in an approximal space between the anterior tooth to be restored and an adjacent anterior tooth.

So constructed, the wedge 400 is specifically designed for use in a dental restoration procedure (e.g., a filling) for an anterior tooth. When it is desired to perform such a dental restoration procedure, the wedge 400 is disposed within an approximal space 480 between an anterior tooth to be restored 482 and an anterior tooth 484 adjacent the anterior tooth to be restored 482, as illustrated in FIG. 4L. The teeth 482, 484 are anterior teeth because each tooth has a buccal-lingual width $W_t$ and a clinical crown height $H_t$ that is greater than the width $W_t$. The wedge 400 is disposed within the approximal space 480 so that the front surface 424 of the body portion 404 and the front surface 442 of the matrix band 406 are facing the anterior tooth to be restored 482, which has a cavity 486 that is adapted to receive a filling during the restoration process. On the other hand, the rear surface 426 of the body portion 404 and the rear surface 444 of the matrix band 406 face the adjacent anterior tooth 484.

When the wedge 400 is so disposed in the approximal space 480, the body portion 404 substantially fills the approximal space 480, and the matrix band 406 contacts the anterior tooth 482, as illustrated in FIG. 4L. More particularly, the front surface 442 of the matrix band 406 contacts the anterior tooth 482, with substantially all of the front surface 442 of the matrix band 406 contacting the anterior tooth 482. Beneficially, because the matrix band 406 has a concave curvature, and the cavity 486 to be filled is convex, the front surface 442 of the matrix band 406 flushly and tightly interlocks with the anterior tooth 482 to be restored. The curvature of the matrix band 406 also properly shapes the contour of the restoration by closely matching or approximating the contours to the natural contours of the anterior tooth to be restored. Furthermore, the curvature of the matrix band 406 allows the matrix band 406 to seal the cavity 486 of the anterior tooth 482, allowing the dentist to fill the cavity 486 while reducing, if not preventing, excess material, but also helps to secure the wedge 400 within the approximal space 480, thereby preventing the wedge 400 from moving from this position while the anterior tooth 482 is being restored. At the same time, the wedge 400, by virtue of its substantially linear shape, will extend linearly through the approximal space 480, such that the wedge will not wrap around the anterior tooth to be restored 482 in a manner that limits the dentist from accessing the cavity 486, as is the case with known products and instruments. Instead, the dentist will have substantially 360 degree access to the cavity 486 during the restoration process.

These technical benefits provided by the wedge 400 are not reachable using any of the existing products and instruments, e.g., the instrument disclosed in the '343 Patent. First, the instrument disclosed in the '343 Patent will not allow for this intimate tooth-matrix band relationship on an anterior tooth. This is due to the fact that the bow shape of the instrument disclosed therein has a much larger radius than the localized curvature of the body portion 404 and matrix band 406. The larger radius of the instrument of the '343 Patent is well-suited for posterior teeth, which have larger radii, while the smaller radii of the body portion 404 and the matrix band 406 makes the wedge 400 well-suited for the smaller radii of anterior teeth. Additionally, in the '343 Patent, the matrix band has a diameter that is greater than its height, is attached to the long bow x-axis, and is bowl shaped, so that the matrix band is not well-suited for restoration of anterior teeth. Furthermore, the instrument disclosed in the '343 Patent, if placed in an approximal space in an anterior region, would not allow 360 degree access as the bow shape of the x-axis of the wedge body and metal band would significantly affect the dentist's vision of working field as well as his/her ability to access the cavitation 486.

Figure 4M:
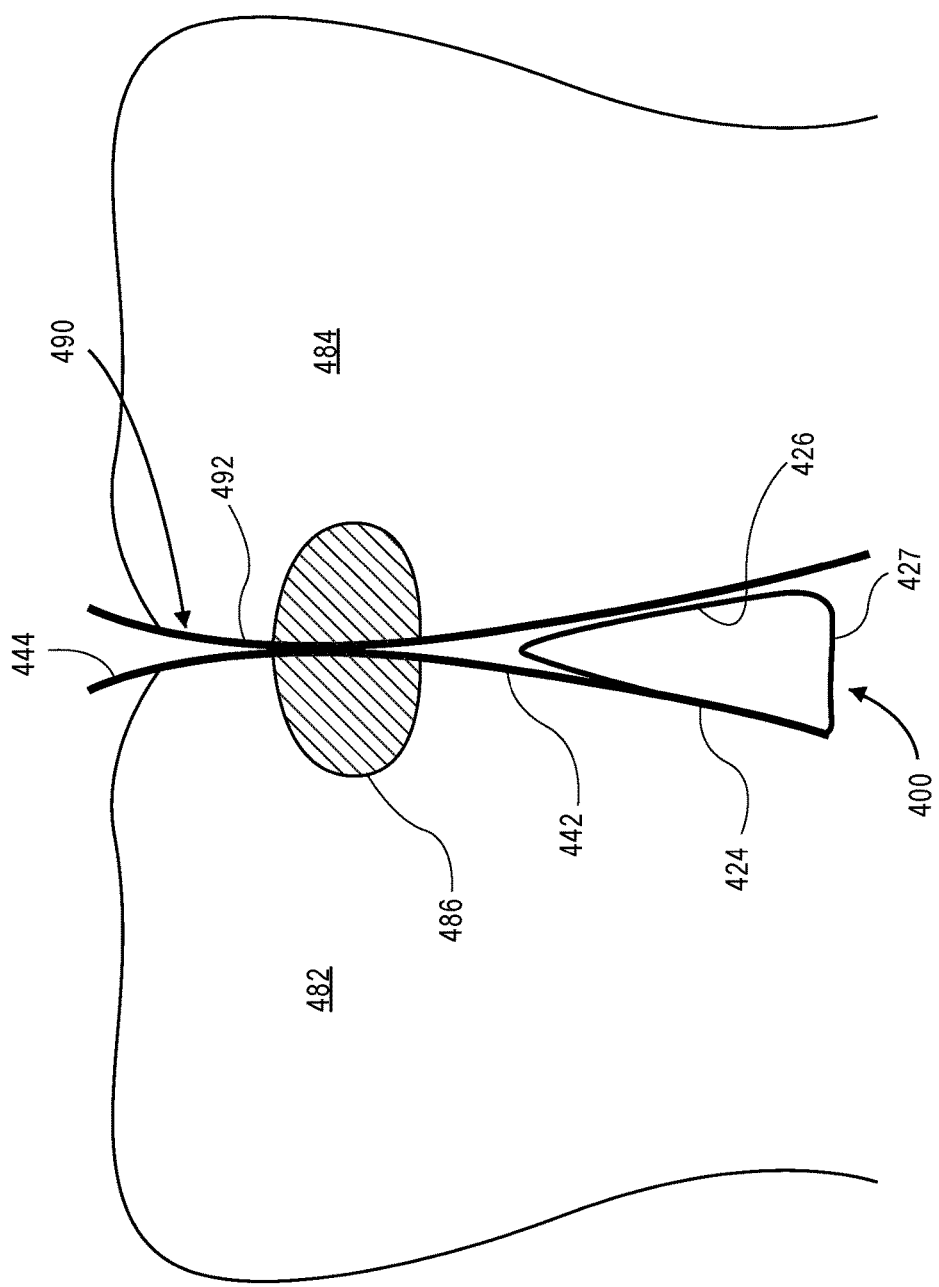
FIG. 4M illustrates an additional matrix band that can be positioned in the approximal space contact with the adjacent anterior tooth while the wedge of FIG. 4A is positioned between the anterior tooth to be restored and the adjacent anterior tooth, thereby allowing for a dental restoration procedure to be simultaneously performed for both the anterior tooth and the adjacent anterior tooth.

An unexpected benefit of the wedge 400 is that the wedge 400 can be utilized in connection with a matrix band 490, substantially similar or identical to the matrix band 406, to allow the dentist to perform a dental restoration procedure on two adjacent anterior teeth that both need to be restored at substantially the same time (i.e., without having to reposition the wedge 400), as illustrated in, for example, FIG. 4M. When the dentist desires to perform a dental restoration procedure on each of two adjacent anterior teeth, e.g., the teeth 480, 482 illustrated in FIG. 4L, the matrix band 490 is first disposed in the approximal space (e.g., approximal space 480) so that a front facing surface 492 of the matrix band 490 contacts one of the teeth to be restored (in this example, the tooth 482). In turn, the wedge 400 can be disposed in the approximal space so that the matrix band 406 of the wedge 400 contacts the other of the teeth to be restored (in this example, the tooth 482). Doing so not only positions the matrix band 406 in the proper position, but also guides the matrix band 490 to its proper position (if not there already) and then securely retains the matrix band 490 in the proper position. With the matrix band 406 in the proper position relative to one of the teeth to be restored and the matrix band 490 in the proper position relative to the other of the teeth to be restored, the dentist can carry out dental restoration procedures on both of the adjacent teeth at substantially the same time.

It will be appreciated that the wedge 400 can be made of one or more suitable materials. In many examples, the handle portion 402 and the body portion 404 will be made of a first material (e.g., wood, a thermoplastic polymer such as polypropylene) and the matrix band 406 will be made of a second material (e.g., metal such as stainless steel, plastic) different from the first material. In other examples, however, the handle portion 402, the body portion 404, and the matrix band 406 may be made of the same material (e.g., a plastic).

Moreover, it will also be appreciated that each anterior tooth has a right side and a left side, which requires that the wedge-band relationship also have a right configuration and a left configuration, respectively. The wedge 400 illustrated in FIGS. 4A-4K is specifically designed as a right-handed wedge for restoring a respective right side of anterior teeth in a human patient's mouth. FIGS. 5A-5D illustrate another example of a wedge 500 that is a mirror image of the wedge 400, such that the wedge 500 is specifically designed for use as a left-handed wedge for restoring a respective left side of anterior teeth in the human patient's mouth.

FIGS. 6A-6Q depict one example of a wedge system 600 that is specifically designed for use in a dental restoration procedure for a posterior tooth. The wedge system 600 in this example includes a pair of wedges—a first wedge 602 and a second wedge 604 that cooperates with the first wedge 602. However, it will be appreciated that the wedge system 600 may, in other examples, only include the first wedge 602. In other words, the wedge system 600 need not include the second wedge 604.

The first wedge 602 is adapted to be disposed in an approximal space between the posterior tooth to be restored and a tooth adjacent the posterior tooth to be restored (the adjacent tooth may also be a posterior tooth), while the second wedge 604 is adapted to be disposed between portions of the first wedge 602 to facilitate proper positioning of the first wedge 602. The first wedge 602 generally includes a handle portion 606, a base element 607 coupled to the handle portion 606, a pair of arms 608A, 608B that are coupled to (e.g., integrally formed with) and extend outward from the base element 606, and a matrix band 610 coupled to the arm 608A. The second wedge 604, meanwhile, includes a handle portion 612 and a body portion 614 that is coupled to (e.g., integrally formed with) and extends outward from the handle portion 612. As will be described in greater detail below, when the first wedge 600 is disposed in the approximal space, the arm 608A and the matrix band 610 are positioned proximate the posterior tooth to be restored and the arm 604B is positioned proximate the adjacent tooth. When the body portion 612 of the second wedge 604 is disposed between portions of the first wedge 602 (in this case, the arms 608A, 608B), the arms 608A, 608B are driven outward, away from one another. The arm 608A, and the matrix band 610 coupled thereto, are forced into intimate contact with the posterior tooth to be repaired, such that a cavity of the posterior tooth to be repaired is sealed while substantially approximating the adjacent tooth. The arm 608B is forced into intimate contact with the adjacent tooth, thereby securely retaining the first wedge 602 in the approximal space. Furthermore, this bi-directional force created by inserting of the second wedge 604 into the first wedge 602 allows the tooth to be restored to be slightly separated from the adjacent tooth. This controlled, slight separation is imperative in creating a proper proximal contact between the restored tooth and the adjacent tooth once the entire system 600 has been removed following the restoration procedure. Thus, the wedge system 600 not only reduces, if not prevents, excess material, thereby reducing finishing time and reducing the failure rate of the dental restoration procedure, but also facilitates the creation of contact points between the posterior tooth and the adjacent tooth, which are desired.

The handle portion 606 of the first wedge 602 generally allows a dentist to grasp the first wedge 602 for the purpose of positioning the wedge 602 in or removing the wedge 602 from the approximal space. The handle portion 606 may have the shape illustrated in FIGS. 6A-6H, or may have any other suitable shape. The handle portion 606 extends from a first end 618 to a second end 620 along a handle axis 622. In other words, the handle portion 606 has a length $L_{h2}$ defined between the first end 618 and the second end 620. In this example, the length $L_{h2}$ is equal to approximately 3.5 mm. In other examples, however, the length $L_{h2}$ can be greater than or less than 3.5 mm. The handle portion 606 also has a height $H_{h2}$ defined between a top side 624 and a bottom side 626 (i.e., perpendicular to the handle axis 622). In this example, the height $H_{h2}$ is equal to approximately 2 mm, though in other examples, the height $H_{h2}$ can be greater than or less than 2 mm.

Figure 6F:
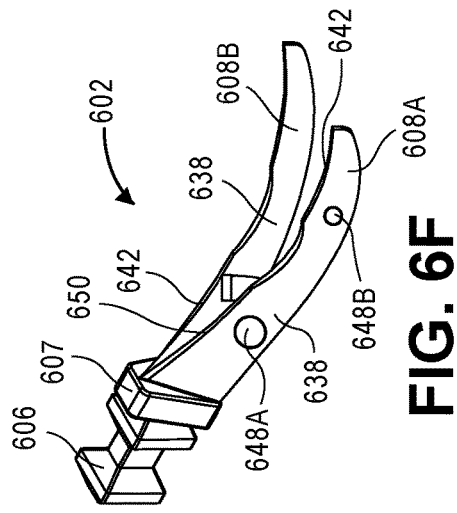
FIG. 6F is a perspective view of a body portion and a handle portion of the wedge of FIG. 6A.
Figure 6I:
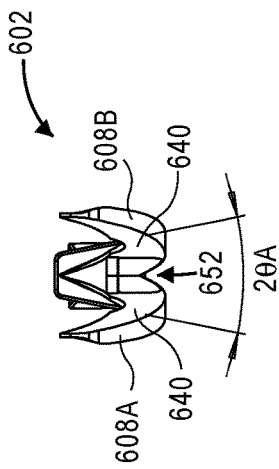
FIG. 6I is an end view of FIG. 6F.
Figure 6G:
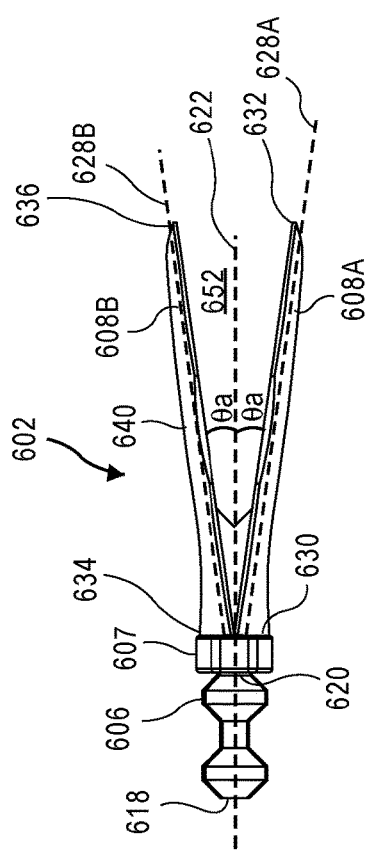
FIG. 6G is a top view of FIG. 6F.
Figure 6H:
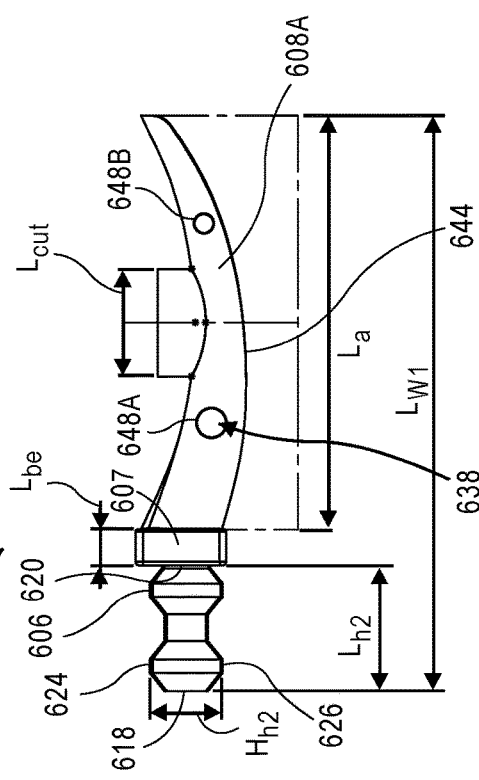
FIG. 6H is a front view of FIG. 6F.

As best illustrated in FIGS. 6F-6H, the base element 607 has a substantially rectangular shape, and the arms 608A, 608B extend outward from the base element 607 along arm axes 628A, 628B, respectively, each oriented at an angle $\theta_a$ relative to the handle axis 622. In this example, the angle $\theta_a$ is equal to approximately 13 degrees, such that the arms 608A, 608B, which extend outward in different directions, are approximately 26 degrees apart from one another. In other examples, however, this angle $\theta_a$ can be a different value between approximately 10 degrees and approximately 15 degrees. More particularly, the arm 608A extends from a first end 630, positioned immediately adjacent the base element 607, to a second end 632, remote from the base element 607, along the arm axis 628A, while the arm 608B extends from a first end 634, positioned immediately adjacent the base element 607 and the first end 630 of the arm 608A, to a second end 636, remote from the base element 607, along the arm axis 628B. It will be appreciated that the distance between the arms 608A, 608B increases as the arms 608A, 608B extend from their respective first ends 630, 634 to their respective second ends 632, 636.

As best illustrated in FIGS. 6F-6I, the arms 608A, 608B are identical in shape and size. Each of the arms 608A, 608B has a substantially triangular, two-shape defined by a substantially triangular front surface 638, a substantially triangular rear surface 640 opposite the front surface 638, and top and bottom surfaces 642, 644 connecting the front and rear surfaces 638, 640. It will be appreciated that the front surfaces 638 of arms 608A, 608B will face the posterior tooth to be restored, and the rear surfaces 640 of arms 608A, 608B will face the posterior tooth when the first wedge 602 is disposed in the approximal space.

The first wedge 602 also includes first and second fastening elements 648A, 648B arranged on one of the arms 608A, 608B (arm 608A, in this case) to securely retain the matrix band 610 thereon. In this example, the fastening elements 648A, 648B each take the form of a circular projection that extends outward from the front surface 638 of the arm 608A. In other examples, however, the first wedge 602 may only include one fastening element, may include more than two fastening elements, may instead include one or more fastening elements on the arm 608B, or may include none at all (e.g., one of the arms 608A, 608B may instead include one or more apertures sized to receive one or more fasteners to secure the matrix band 610 to one of the arms 608A, 608B).

As best illustrated in FIG. 6H, the arm 608A has a length $L_a$ defined between the first end 630 and the second end 632 and along the arm axis 628A. The length $L_a$ is preferably in a range of between approximately 7.5 mm and approximately 13 mm, with the total length $L_{w1}$ of the first wedge 602 in a range of between approximately 12 mm and approximately 18 mm. In this example, the length $L_a$ is equal to approximately 11.5 mm, and the base element 607 has a length $L_{be}$ equal to approximately 1 mm, such that the total length $L_{w1}$ of the first wedge 602 is equal to approximately 16 mm. In other examples, however, the length $L_a$ can be greater than or less than 11.5 mm, with the total length $L_{w1}$ of the wedge 602 being greater than or less than approximately 16 mm. In any case, the arm 608A in this example has a thickness, defined herein as the distance between the front and rear surfaces 638, 640, that slightly decreases as the arm 608A extends from the first end 630 to the second end 632, as illustrated in FIG. 6G. In other examples, however, the arm 608A may have a constant thickness or may taper to a greater degree than what is shown in FIG. 6H.

As also best illustrated in FIG. 6H, the arm 608A has a height, defined herein as the distance between the top and bottom surfaces 642, 644, that decreases or tapers as the arm 608A extends from the first end 630 to the second end 632. FIG. 6H also illustrates that the arm 608A curves downward before curving upward again as the arm 608A extends from the first end 630 to the second end 632. In this example, the arm 608A curves upward to a greater degree than it curves downward, such that a central point of the second end 632 is positioned further upward than a central point of the first end 630. Additionally, a cutout 648 is formed in the arm 608A along the top surface 642. In this example, the cutout 648 is a circular cutout and has a length $L_{cut}$ that is equal to 3 mm. In other examples, however, the cutout can have a different shape and/or size. As an example, the length $L_{cut}$ can be greater than or less than 3 mm.

In the interest of brevity, the preceding two paragraphs only discuss features of the arm 608A. However, because the arm 608B is identical in shape and size to the arm 608A, it will be appreciated that the arm 608B has the same features. In other words, the arm 608B has a length, height, and curvature that is identical to the arm 608B.

As illustrated in FIGS. 6G-6I, the first wedge 602 also includes a wing 650 that is arranged between the base element 607 and the arms 608A, 608B to help keep the arms 608A, 608B a desired distance from one another. The wing 650 has a curvature that generally matches the curvature of the arms 608A, 608B. More particularly, the wing 650 extends downward from the base element 650 and along a portion of the top surface 644 of each of the arms 608A, 608B, as best illustrated in FIGS. 6F and 6I. Thus, like the arms 608A, 608B, the wing 650 in this example also has a substantially triangular shape. In other examples, however, the wing 650 can have a different shape and/or size.

Additionally, the first wedge 650 includes a gap 652 that is formed or defined between the arms 608A, 608B, and, at least in this example, the wing 650. The gap 652 is generally sized to receive the second wedge 604, particularly the body portion 614 of the second wedge 604, as will be discussed in greater detail below. And because the distance between the arms 608A, 608B increases as the arms 608A, 608B extend from their respective first ends 630, 634 to their respective second ends 632, 636, the size of the gap 652 also increases as the arms 608A, 608B extend from their respective first ends 630, 634 to their respective second ends 632, 636.

As illustrated in FIGS. 6J-6M, the matrix band 610 of the first wedge 602 has a thin, substantially trapezoidal profile that is defined by a front surface 654, a rear surface 656 opposite the front surface 654, and a thickness $T_{m1}$ between the front and rear surfaces 654, 656. The front surface 654 is arranged to face (and engage) the posterior tooth to be restored, while the rear surface 656 is arranged to face the tooth adjacent the posterior tooth to be restored, when the first wedge 602 is in use. As also illustrated in FIGS. 6J-6M, the matrix band 610 generally extends from a first end 658 to a second end 660 along a height axis 662 and generally extends from a first side 664 to a second side 666 along a length axis 668. As best illustrated in FIG. 6L, the matrix band 610 has a slight, gradual, and smooth concave curvature along and away from the height axis 662. As best illustrated in FIG. 6M, the matrix band 610 has a slight, gradual, and smooth concave curvature along the length axis 668. In this example, the matrix band 610 has a radius of curvature R of 40 mm, though in other examples, the radius of curvature R can be any value in a range of between 32 mm and 48 mm. In any case, it will be appreciated that portions of the matrix band 610 between the first and second sides 664, 666 are slightly offset from the length axis 668.

It will be appreciated from FIGS. 6J and 6K that the matrix band 610 has a height $H_{m2}$ and a length $L_{m2}$ that is greater than the height $H_{m2}$. In other words, the matrix band 610 has a incisal-gingival dimension and a buccal-lingual dimension that is larger than the incisal-gingival dimension. The height $H_{m2}$ of the matrix band 610 is preferably in a range between approximately 3 mm and approximately 6.5 mm, while the length $L_{m2}$ of the matrix band 610 is preferably in a range between approximately 4.5 mm and approximately 11 mm. Thus, in some examples, the length $L_{m2}$ of the matrix band 610 may be at least twice as large as the height $H_{m2}$ of the matrix band 610. In this example, the height $H_m$ of the matrix band 610 is 5 mm, and the length $L_m$ of the matrix band 610 is 9 mm. It will also be appreciated from FIGS. 6K and 6L that the thickness $T_{m2}$ of the matrix band 610 is considerably smaller than the height $H_{m2}$ and the length $L_{m2}$ of the matrix band 610. In this example, the thickness $T_{m2}$ is equal to 0.05 mm, though the thickness $T_{m2}$ can vary between approximately 0.025 mm and approximately 0.05 mm.

With the arms 608A, 608B and the matrix band 610 so dimensioned, the arm 608A is configured to engage, retain, and support the matrix band 610. More particularly, the curvature of the arm 608A allows the matrix band 610 to maintain a matching curvature. This curvature of both the arm 608A and the matrix band 610 further allows the first wedge 602 to engage with the convex surface of the posterior tooth to be restored when inserted into the approximal space and utilized with the second wedge 604. The matrix band 610 is coupled to the arm 608A so that the rear surface 658 of the matrix band 610 faces, and at least partially contacts, the front surface 638 of the arm 608A. In this example, the matrix band 610 is coupled to the arm 608A via the first and second fastening elements 648A, 648B, which are received in first and second similarly shaped apertures 670, 672, respectively, formed in the rear surface 658 of the matrix band 610. In this example, the distance $D_a$ between the apertures 670, 672 is approximately 7.5 mm, though this distance can vary. The fastening elements 648A, 648B may be secured therein in any known manner. In other examples, the matrix band 610 may be coupled to the arm 608A via one fastening element, more than two fastening elements, or in some other manner. In any case, when the matrix band 610 is coupled to the arm 608A, as shown in FIGS. 6A-6E, the height axis 454 is angled relative to both the handle axis 622 and the arm axis 628A.

Turning now to FIGS. 6N-6Q, further details regarding the second wedge 604 will now be described. At the outset, it will be appreciated that the second wedge 604 is substantially similar to the wedge 400, in that the wedge 604 includes a handle portion 702 and a body portion 704, but the wedge 604 does not include a matrix band. The handle portion 702 is identical to the handle portion 402 described above. Thus, in the interest of brevity, the handle portion 702 will not be discussed in further detail. The body portion 704 is similar to the body portion 404 described above, with the exception of the differences discussed below.

First, unlike the body portion 404, which has a substantially triangular shape defined by the surfaces 424, 426, and 427, the body portion 704 has a substantially triangular shape defined by a substantially triangular front surface 724, a substantially triangular rear surface 726 opposite the front surface 724, and a substantially triangular top surface 728 that connects the front and rear surfaces 724, 726. The body portion 704 also has a hollow, V-shaped area 730 defined or formed between the surfaces 724, 726, and 728, as best illustrated in FIG. 6Q. It will be appreciated that the V-shaped area 730 allows the second wedge 604 to effectively act as a biasing element (e.g., a spring) when the second wedge 604 is disposed in the first wedge 602, by driving the arms 608A, 608B outward, toward the desired position.

Second, the dimensions of the body portion 704 vary from the dimensions of the body portion 404. As best illustrated in FIG. 6O, the body portion 404 has a length $L_{b2}$ defined between a first end 720 and a second end 722 and along a body axis 723. In this example, the length $L_{b2}$ is equal to approximately 8.5 mm, such that the total length $L_{w2}$ of the second wedge 604 is equal to approximately 12 mm. In other examples, however, the length $L_{b2}$ can be greater than or less than 8.5 mm, with the total length $L_{w2}$ of the wedge 604 being greater than or less than approximately 12 mm (e.g., the total length $L_{w2}$ can be in a range of between 10 mm and 15 mm). In any case, the body portion 704 has a thickness, defined herein as the distance between the front and rear surfaces 724, 726, that decreases as the body portion 704 extends from the first end 720 to the second end 722. In this example, the thickness $T_{fe2}$ at the first end 720 is equal to approximately 1.25 mm, the thickness $T_{2p}$ at a point 732 located between the first and second ends 720, 722 is equal to approximately 1.15 mm, the thickness $T_{2p2}$ at another point 733 located between the first and second ends 720, 722 is equal to approximately 0.90 mm, and the thickness $T_{se2}$ at the second end 720 is equal to approximately 0.40 mm. In other examples, however, these thickness values may vary. As an example, the thickness $T_{fe2}$ may be greater than approximately 1.25 mm but less than 2.0 mm, the thickness $T_{2p}$ may be greater than approximately 1.15 mm but less than 1.9 mm, and the thickness $T_{2p2}$ may be greater than approximately 0.90 mm but less than 1.65 mm. The body portion 704 also has a height that decreases or tapers as the body portion 704 extends from the first end 720 to the second end 722, such that the bottom of the body portion 704 is angled relative to the horizontal (see FIG. 6O), which may help to position the wedge 604 within the approximal space. In this example, the height $H_{fe2}$ at the first end 720 is equal to approximately 2 mm, the height $H_{2p1}$ at a first point 736 between the first end 720 and the second end 722 is equal to approximately 1.72 mm, and the height $H_{2p2}$ at a second point 738 also between the first and second ends 720, 722 is equal to approximately 1.48 mm. In other examples, however, these height values may vary.

Figure 6R:
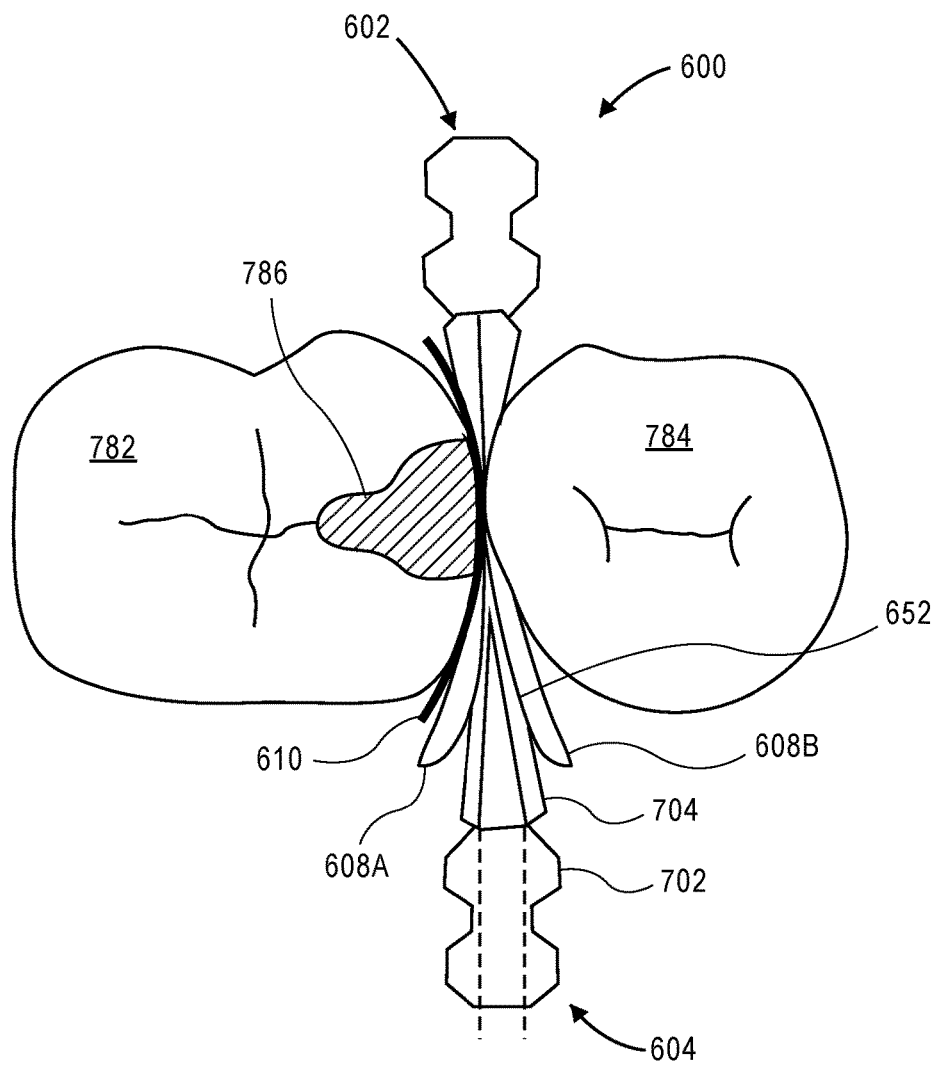
FIG. 6R is a top view showing the wedge of FIG. 6A and the wedge of FIG. 6N positioned in an approximal space between the posterior tooth to be restored and an adjacent posterior tooth.
Figure 6S:
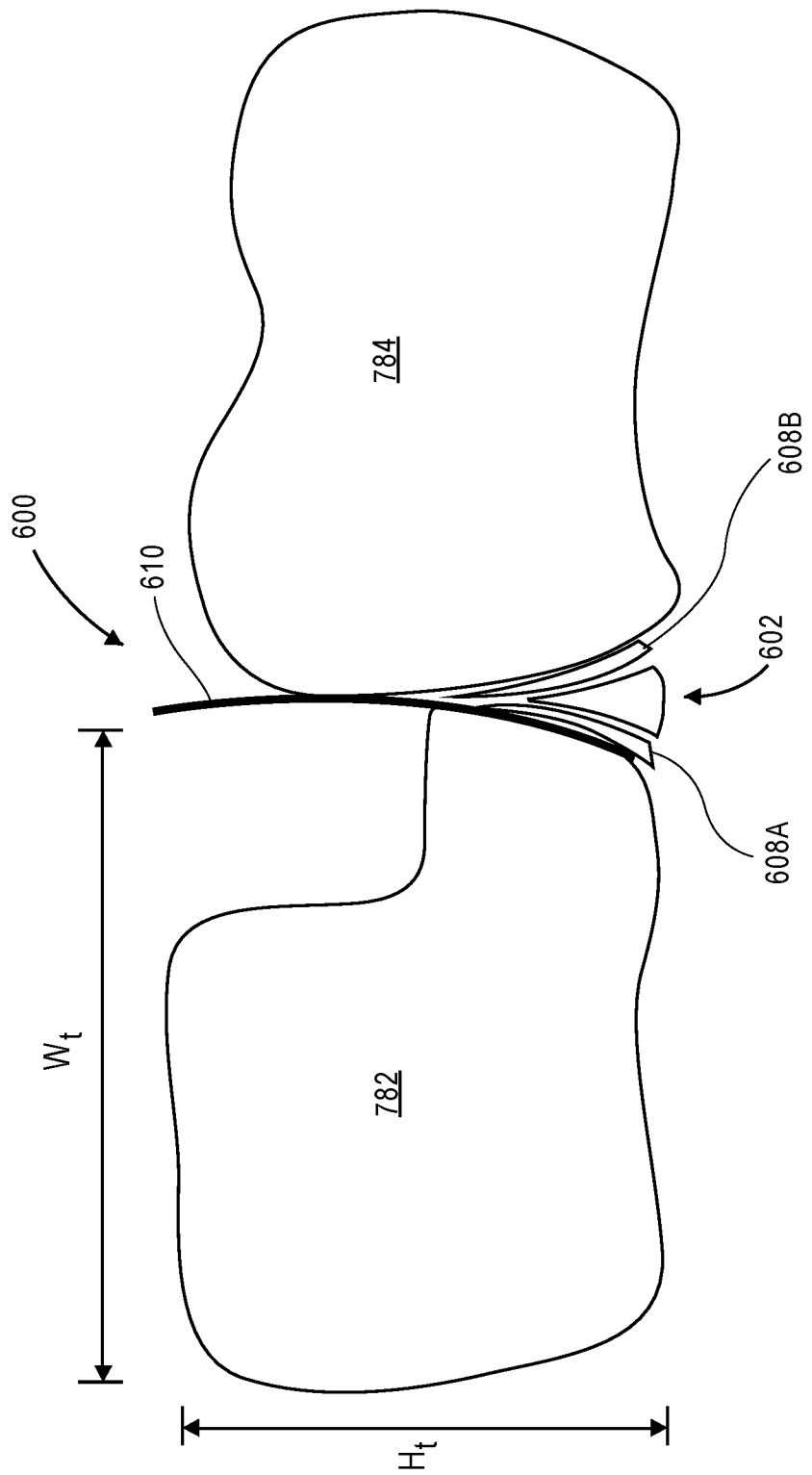
FIG. 6S is a side view of FIG. 6R.

So constructed, the wedge system 600 is specifically designed for use in a dental restoration procedure (e.g., a filling) for a posterior tooth. When it is desired to perform such a dental restoration procedure, the first wedge 602 is disposed within an approximal space between a posterior tooth to be restored 782 and an posterior tooth 784 adjacent the posterior tooth to be restored 782, as illustrated in FIGS. 6R and 6S. The teeth 782, 784 are posterior teeth because each tooth has a buccal-lingual width $W_t$ and a clinical crown height $H_t$ that is less than or equal to the width $W_t$. The first wedge 602 is disposed within the approximal space so that the front surface 638 of the arm 608A and the front surface 654 of the matrix band 610 are facing the posterior tooth to be restored 782, which has a cavity 786 that is adapted to receive a filling during the restoration process. On the other hand, the rear surface 640 of the arm 608A and the rear surface 656 of the matrix band 610 face the adjacent posterior tooth 784.

Before, after, or at the same time as the first wedge 602 is positioned within the approximal space, the second wedge 604 is positioned within the approximal space. The first and second wedges 602, 604 are positioned so that the second wedge 604 is disposed in the gap 652. More particularly, the body portion 704 of the second wedge 604 is disposed in the gap 652, between the arms 608A, 608B, and below the wing 650, as best illustrated in FIG. 6R. When the second wedge 604 is so positioned, the arms 608A, 608B are driven outward, away from one another, by the body portion 704 (particularly the surfaces 724, 726). The arm 608A and the matrix band 610 are driven into intimate contact with the posterior tooth to be restored 782, while the arm 608B is driven into intimate contact with the adjacent tooth 784. More particularly, the front surface 654 of the matrix band 610 contacts the posterior tooth to be restored 782, with substantially all of the front surface 654 of the matrix band 610 contacting the posterior tooth 782.

Beneficially, because the matrix band 610 has a concave curvature, and the cavity 786 to be filled is convex, the front surface 654 of the matrix band 610 flushly and tightly interlocks with the posterior tooth to be restored 782, as illustrated in FIGS. 6R and 6S. The curvature of the matrix band 610 also properly shapes the contour of the restoration by closely matching or approximating the contours to the natural contours of the posterior tooth to be restored. Furthermore, the curvature of the matrix band 610 allows the matrix band 610 to seal the cavity 786 of the posterior tooth 782, allowing the dentist to fill the cavity 786 while reducing, if not preventing, excess material, but also helps to secure the wedge 602 within the approximal space, thereby preventing the wedge 602 from moving from this position while the posterior tooth 782 is being restored. This is also helped by the fact that the second wedge 604 is disposed in the gap 652 of the first wedge 602.

Moreover, it will also be appreciated that each anterior tooth has a right side and a left side, which requires that the wedge-band relationship also have a right configuration and a left configuration, respectively. The wedge system 600 illustrated in FIGS. 6A-6P is specifically designed as a right-handed wedge for restoring a respective right side of posterior teeth in a human patient's mouth. While not illustrated, it will be appreciated that the wedge system 600 can be inverted so as to be specifically designed for use as a left-handed wedge for restoring a respective left side of posterior teeth in the human patient's mouth.

Throughout this specification, structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The invention claimed is:

1. A wedge system for use in a dental restoration procedure for a posterior tooth, comprising:
 a first wedge adapted to be disposed in an approximal space between the posterior tooth and a tooth adjacent the posterior tooth, the first wedge including a body, a first arm extending from the body, a second arm extending from the body, a wing connecting the first arm and the second arm, and a gap formed below the wing and between the first arm and the second arm, wherein the first and second arms extend outward from the wing; and a second wedge including a body and an arm extending from the body of the second wedge, wherein at least a portion of the arm of the second wedge is arranged to be disposed in the gap of the first wedge to removably secure the second wedge to the first wedge, wherein when the at least the portion of the arm of the second wedge is disposed in the gap of the first wedge, the body of the first wedge extends along a first longitudinal axis and the body of the second wedge extends along a second longitudinal axis that is substantially coaxial with the first longitudinal axis.

2. The wedge system of claim 1, wherein the first arm extends from the body along a first axis and the second arm extends from the body along a second axis that is angled relative to the first axis.

3. The wedge system of claim 1, wherein the first wedge further comprises a handle extending outward from the body.

4. The wedge system of claim 1, wherein when the arm of the second wedge is disposed in the gap of the first wedge, the arm of the second wedge forces the first and second arms of the first wedge away from one another.

5. The wedge system of claim 1, wherein the second wedge has an angled bottom surface arranged to facilitate insertion of the second wedge into an approximal space between the posterior tooth and a tooth adjacent the posterior tooth.

6. The wedge system of claim 1, further comprising a matrix band coupled to and extending outward from the first arm or the second arm of the first wedge.

7. The wedge system of claim 6, further comprising a cutout arranged in the first arm to improve adaptation of the matrix band wedge unit to the posterior tooth.

8. The wedge system of claim 1, wherein when the first wedge is disposed in the approximal space and the at least the portion of the arm of the second wedge is disposed in the gap of the first wedge, the body of the second wedge is disposed in the approximal space.

9. The wedge system of claim 1, wherein when the at least the portion of the arm of the second wedge is disposed in the gap of the first wedge, the second wedge is disposed entirely between outer surfaces of the first and second arms of the first wedge.

10. A wedge system for use in a dental restoration procedure for a posterior tooth, comprising:
a first wedge adapted to be disposed in an approximal space between the posterior tooth and a tooth adjacent the posterior tooth, the first wedge including a body, a first arm extending from the body, a second arm extending from the body, and a gap formed between the first arm and the second arm;
a matrix band coupled to and extending outward from the first arm or the second arm of the first wedge; and
a second wedge including a body and an arm extending from the body of the second wedge, wherein at least a portion of the arm of the second wedge is arranged to be disposed in the gap of the first wedge to removably secure the second wedge to the first wedge,
wherein when the first wedge is disposed in the approximal space and the at least the portion of the arm of the second wedge is disposed in the gap of the first wedge, the body of the second wedge is disposed in the approximal space.

11. The wedge system of claim 10, wherein the first arm extends from the body of the first wedge along a first axis and the second arm extends from the body of the first wedge along a second axis that is angled relative to the first axis.

12. The wedge system of claim 10, wherein the first wedge further comprises a handle extending outward from the body of the first wedge.

13. The wedge system of claim 10, wherein when the arm of the second wedge is disposed in the gap of the first wedge, the arm of the second wedge forces the first and second arms of the first wedge away from one another.

14. The wedge system of claim 10, further comprising a cutout arranged in the first arm to improve adaptation of the matrix band to the posterior tooth.

15. The wedge system of claim 10, further comprising a wing connecting the first arm and the second arm.

16. The wedge system of claim 10, wherein the second wedge has an angled bottom surface arranged to facilitate insertion of the second wedge into an approximal space between the posterior tooth and a tooth adjacent the posterior tooth.

17. The wedge system of claim 10, wherein when the at least the portion of the arm of the second wedge is disposed in the gap of the first wedge, the body of the first wedge extends along a first longitudinal axis and the body of the second wedge extends along a second longitudinal axis that is substantially coaxial with the first longitudinal axis.

18. A method of preparing a posterior tooth for a dental restoration procedure, the method comprising:
providing a first wedge including a body, a first arm extending from the body, a second arm extending from the body, a wing connecting the first arm and the second arm, and a gap formed below the wing and between the first arm and the second arm, wherein the first and second arms extend outward from the wing;
inserting the first wedge into an approximal space between the posterior tooth and a tooth adjacent to the posterior tooth;
providing a second wedge including a body and an arm extending from the body of the second wedge; and
after the first wedge is inserted into the approximal space, inserting the second wedge into the approximal space such that at least a portion of the arm of the second wedge is disposed in the gap of the first wedge, thereby removably securing the second wedge to the first wedge, wherein when the at least the portion of the arm of the second wedge is disposed in the gap of the first wedge, the body of the first wedge extends along a first longitudinal axis and the body of the second wedge extends along a second longitudinal axis that is substantially coaxial with the first longitudinal axis.

19. The method of claim 18, wherein disposing at least the portion of the arm of the second wedge in the gap of the first wedge comprises driving the first arm of the first wedge toward the posterior tooth and driving the second arm of the first wedge away from the first arm and toward the tooth adjacent the posterior tooth.

* * * * *

UNITED STATES PATENT AND TRADEMARK OFFICE
CERTIFICATE OF CORRECTION

| | | |
|---|---|---|
| PATENT NO. | : 10,238,470 B2 | Page 1 of 1 |
| APPLICATION NO. | : 15/727548 | |
| DATED | : March 26, 2019 | |
| INVENTOR(S) | : Matthew Burton | |

It is certified that error appears in the above-identified patent and that said Letters Patent is hereby corrected as shown below:

In the Claims

At Column 19, Line 36, "band wedge unit to" should be -- band to --.

Signed and Sealed this
Twenty-first Day of April, 2020

Andrei Iancu
*Director of the United States Patent and Trademark Office*